United States Patent
Snyder et al.

(10) Patent No.: US 7,655,224 B2
(45) Date of Patent: *Feb. 2, 2010

(54) NEURAL STEM CELLS AND USE THEREOF FOR BRAIN TUMOR THERAPY

(75) Inventors: Evan Y. Snyder, La Jolla, CA (US); Xandra O. Breakefield, Newton Center, MA (US); Karen S. Aboody, Arcadia, CA (US); Ulrich Herrlinger, Tuebingen (DE); William P. Lynch, Ravenna, OH (US)

(73) Assignees: Children's Medical Center Corp., Boston, MA (US); The General Hospital Corp., Boston, MA (US); Northeastern Ohio Universities COM, Rootstown, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 11/546,726

(22) Filed: Oct. 12, 2006

(65) Prior Publication Data

US 2007/0031391 A1 Feb. 8, 2007

Related U.S. Application Data

(63) Continuation of application No. 09/795,675, filed on Feb. 28, 2001, now Pat. No. 7,186,409, which is a continuation-in-part of application No. 09/168,350, filed on Oct. 7, 1998, now abandoned, which is a continuation-in-part of application No. 09/133,873, filed on Aug. 14, 1998, now Pat. No. 5,958,767.

(60) Provisional application No. 60/185,572, filed on Feb. 28, 2000.

(51) Int. Cl.
*A61K 48/00* (2006.01)
*C12N 15/63* (2006.01)
*C12N 5/08* (2006.01)
*A61K 31/70* (2006.01)

(52) U.S. Cl. .......... 424/93.21; 435/455; 435/320.1; 435/368

(58) Field of Classification Search ............ None
See application file for complete search history.

(56) References Cited

U.S. PATENT DOCUMENTS

| | | | |
|---|---|---|---|
| 5,585,096 A * | 12/1996 | Martuza et al. | ........ 424/93.2 |
| 5,624,830 A | 4/1997 | Mullen et al. | |
| 5,750,376 A | 5/1998 | Weiss et al. | |
| 5,753,506 A | 5/1998 | Jobe | |
| 5,851,832 A | 12/1998 | Weiss et al. | |
| 6,258,353 B1 * | 7/2001 | Isacson et al. | ........ 424/93.1 |
| 6,969,608 B1 * | 11/2005 | Miller et al. | ........ 435/325 |
| 2002/0006660 A1 * | 1/2002 | Sabate et al. | ........ 435/325 |

OTHER PUBLICATIONS

Park et al. Global gene and cell replacement strategies via stem cells. Gene therapy 9:613-624, 2002.*
Noble, M. Can neural stem cells be used to track down and destroy migratory brain tumor cells while also providing a menas of repairing tumor-associated damage? PNAS 97:12393-12395, 2000.*
Noble, M. Can neural stem cells be used as therapeutic vehicles in the treatment of brain tumors? Nature Medicine 6:369-370, 2000.*
Randazzo et al. Treatment of experimental intracranial murine melanoma with a neuroattenuated herpes simplex virus 1 mutant. Virology 211:94-101, 1996.*
Snyder, E., et al., *Nature* (London) 374:367-370, 1995.
Weiss, S., et al., *Trends Neurosci.*19:387-393, 1996.
McKay, R., *Science* 276:66-71, 1997.
Snyder, E., et al., *Proc. Natl. Acad. Sci. USA* 94:11663-11668, 1997.
Flax, J.D., et al., *Nat. Biotech.* 16: 1033-1039, 1998.
Topf, N., et al., *Gene Ther.* 5:507-513, 1998.
Cage, et al. *Am. Rev. Neurosci.* 18:159-192, 1995.
Wittemore, et al., *Molecular Neurobiology* 12:13-39, 1996.
Snyder, *The Neuroscientist* 4:408-425, 1998.
Snyder, et al., *Cell* 68:33-51, 1992.
Renfranz, et al., *Cell* 66:713-729, 1991.
Snyder, et al., *Current Opin. In Pediatrics* 8:558-568, 1996.
Park, J. *Neurotrauma* 16:675-687,1999.
Aboody-Guterman, et al., *Neuro Report* 8:3801-3808, 1997.

* cited by examiner

*Primary Examiner*—Quang Nguyen
(74) *Attorney, Agent, or Firm*—Nixon Peabody LLP

(57) ABSTRACT

The present invention is based upon a surprising finding that stem cells, more particularly neural stem cells, can migrate throughout a brain tumor and track metastatic brain tumor cells. The invention provides a method for treating brain tumors by administering genetically engineered neural stem cells in an individual affected by brain tumors. The invention also provides a method of preparing genetically engineered neural stem cells and a composition comprising genetically engineered neural stem cells in a pharmaceutically acceptable carrier.

5 Claims, 6 Drawing Sheets

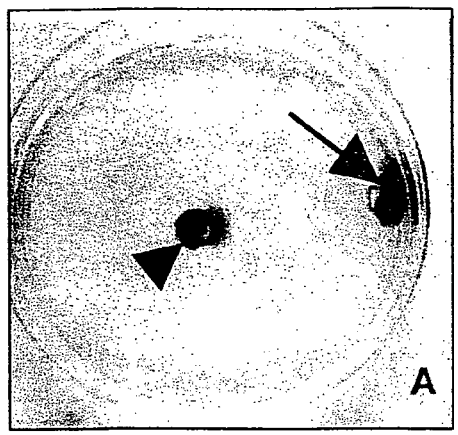
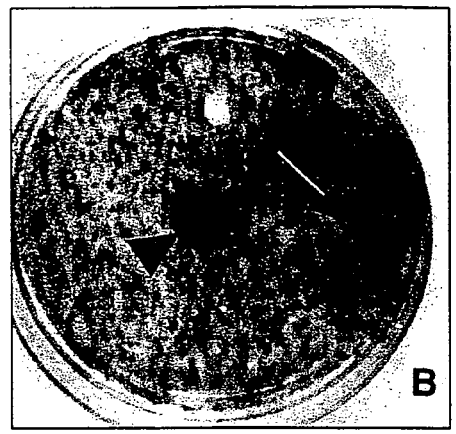
FIG. 1A  FIG. 1B
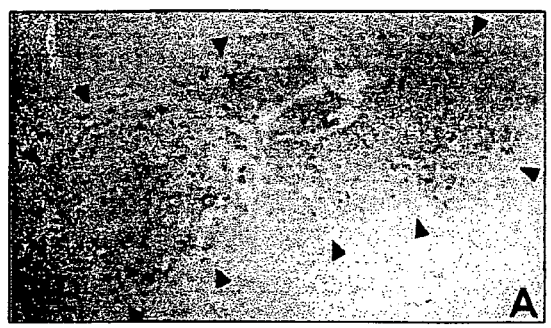
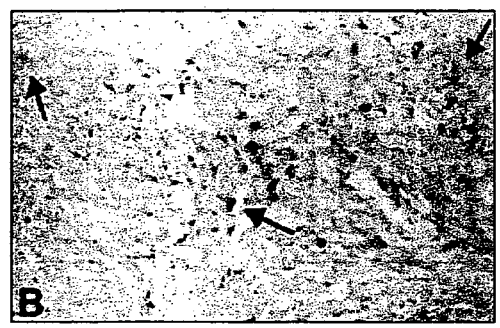
FIG. 2A  FIG. 2B
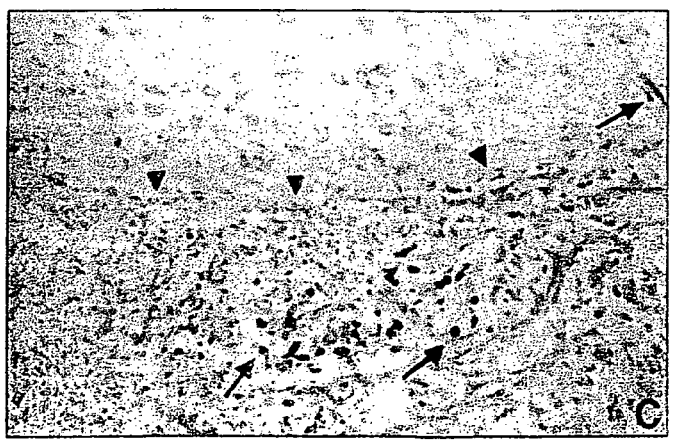
FIG. 2C  FIG. 2D

NEURAL STEM CELLS AND USE THEREOF FOR BRAIN TUMOR THERAPY

RELATED APPLICATIONS

This application is a continuation of U.S. application Ser. No. 09/795,675 filed Feb. 28, 2001, which claims the benefit under 35 U.S.C. §119(e) of U.S. Provisional Application Ser. No. 60/185,572, filed on Feb. 28, 2000; and the application is also a continuation-in-part of U.S. application Ser. No. 09/168,350 filed on Oct. 7, 1998, which is a continuation-in-part of U.S. application Ser. No. 09/133,873, filed on Aug. 14, 1998, now U.S. Pat. 5,958,767.

GOVERNMENT SUPPORT

This invention was made in part with support from the National Institutes of Health under grant number NIH P20-HD18655, and the United States government has certain rights in this invention.

BACKGROUND OF THE INVENTION

1. Field of the Invention

This invention is in the field of gene therapy, more particularly the field of using neuronal cells to treat brain tumors. The present invention further relates to the field of genetic engineering and medical treatment with genetically engineered stem cells. More particularly, the invention relates to a method of treatment of CNS tumors using genetically engineered neural stem cells (NSCs).

2. Technical Background

An effective gene therapy for the treatment of brain tumors has been an elusive goal for many years. Glioblastoma multiforma, which is virtually untreatable, and the less malignant anaplastic astrocytoma account for about one-quarter of the 5,000 intracranial gliomas diagnosed yearly in the United States; 75 percent of gliomas in adults are of this category. Because of its profound and uniform morbidity, it contributes more to the cost of cancer on a per capita basis than does any other tumor. The patient, commonly stricken in the fifth decade of life, enters a cycle of repetitive hospitalizations and operations while experiencing the progressive complications associated with relatively ineffective treatments of radiation and chemotherapy ["Harrison's Principles of Internal Medicine," edited by Issetbacher, Braunwald, Wilson, Martin, Fauci and Kasper, 13th Edition, p. 2262, McGraw-Hill, Inc. 1994].

One of the impediments to gene therapy of brain tumors such as gliomas, has been the degree to which they expand, migrate widely and infiltrate normal tissue. Most gene therapy strategies to date are viral vector-based, yet extensive distributions of sufficient amounts of viral vector-mediated genes to large regions and numbers of cells typically in need has often been disappointingly limited. Interestingly, one of the defining features of normal neural progenitors and stem cells is their migratory quality. Neural stem cells (NSCs) are immature, uncommitted cells that exist in the developing, and even adult, CNS and postulated to give rise to the array of more specialized cells of the CNS. They are operationally defined by their ability to self-renew and to differentiate into cells of most (if not all) neuronal and glial lineages in multiple anatomical & development contexts, and to populate developing and/or degenerating CNS regions [Ciage et al., *Ann Rev Neurosci* 18: 159-92, 1995; Whittemore et al., *Molecular Neurobiology* 12:13-39 1996; McKay *Science* 276: 66-71, 1997; Gage F H, Christen Y. (eds.), *Research & Perspecti'ves in Nourotciences: Isolation, Characterization, & Utilization of CNS Stem Cells*, Springer-Verlag, Heidelberg, Berlin, 1997; Snyder, *The Neuroscientist* 4, 408-25, 1998].

With the first recognition that neural cells with stem cell properties, reproduced in culture, could be reimplanted into mammalian brain where they could reintegrate appropriately and seamlessly in the neural architecture and stably express foreign genes gene therapists began to speculate how such a phenomenon might be harnessed for therapeutic purposes [Snyder et al., *Cell* 68: 33-51 1992; Renfranz et al., *Cell* 66: 713-729, 1991]. These, and the studies which they spawned, provided hope that the use of neural progenitor/stem cells, by virtue of their inherent biology, might circumvent some of the present limitations of presently available gene transfer vehicles (e.g., non-neural cells, viral vectors, synthetic pumps), and provide the basis for a variety of novel therapeutic strategies [for review, see e.g., [Ciage et al., *Ann Rev Neurosci* 18: 159-92, 1995; Whittemore et al., *Molecular Neurobiology* 12:13-39 1996; McKay *Science* 276: 66-71, 1997; Gage F H, Christen Y. (eds.), *Research & Perspecti'ves in Nourotciences: Isolation, Characterization, & Utilization of CNS Stem Cells*, Springer-Verlag, Heidelberg, Berlin, 1997; Snyder, *The Neuroscientist* 4: 408-25, 1998; Snyder et al., *Current Opin in Pediatrics* 8: 558-568, 1996].

The use of neural stem cells as graft material has been clearly illustrated by the prototypical neural progenitor clone, C17.2, a clone with which we have had extensive experience which was used in the studies presented here [Snyder et al., *Cell* 68: 33-51 1992; Snyder et al., *Nature* 374: 367-370, 1995; Park, *J Neurotrauma* 16: 675-87, 1999; Aboody-Guterman et al., *NeuroReport* 8: 3801-08, 1997]. C17.2 is a mouse cell line from postnatal day 0 cerebellum immortalized by infection with a retroviral construct containing the avian myc gene. This line has been transduced to constitutively express the lacZ and neoR genes. When transplanted into germinal zones throughout the brain, these cells have been shown to migrate, cease dividing, and participate in the normal development of multiple regions at multiple stages (fetus to adult) along the murine neuraxis, differentiating appropriately into diverse neuronal and glial cell types as normal, nontumorigenic cytoarchitectural constituents. They intermingle non-disruptively with endogenous neural progenitor/stem cells, responding to the same spatial and temporal cues in a similar manner. Crucial for therapeutic considerations, the structures to which C17.2 cells contribute develop and maintain neuroanatomical normality. In their earliest therapeutic use, they served to deliver a missing gene product throughout the brains of mice with a lysosomal deficiency state and cross-corrected host cells by release and uptake of a lysosomal enzyme [Snyder et al., *Nature* 374: 367-370, 1995]. The feasibility of a neural progenitor/stem cell-based strategy for the delivery of therapeutic molecules directly to and throughout the CNS was first affirmed by correcting the widespread neuropathology of a murine model of the genetic neurodegenerative lysosomal storage disease mucopolysaccaridosis type VII, caused by an inherited deletion of the β-glucuronidase (GUSB) gene, a condition that causes mental retardation and early death in humans. Exploiting their ability to engraft diffusely and become integral members of structures throughout the host CNS, GUSB-secreting NSCs were introduced at birth into subventricular germinal zone, and provided correction of lysosomal storage in neurons and glia throughout mutant brains. In so doing, it established that neural transplantation of neural progenitor cells could provide a novel therapeutic modality.

What is needed is a way to treat tumors which are diffuse, infiltrating and/or metastasizing. What is needed is a way to treat tumors locally to maximize the impact on the tumor and reduce the toxicity to the patient.

SUMMARY OF THE INVENTION

An isolated pluripotent neuronal cell having the capacity to differentiate into at least different types of nerve cells is disclosed. The pluripotent cell is further characterized by having a migratory capacity whereby the cell is capable of traveling from a first location where the neuronal cell is administered to a second location at which there is at least one tumor cell, having the ability to travel through and around a tumor, whereby a plurality of the neuronal cells are capable of surrounding the tumor; and having the capacity to track at least one infiltrating tumor cell, thereby treating infiltrating and metastasizing tumors.

The neuronal cell may be an isolated neural stem cell. The neuronal cell can be genetically engineered to secrete a cytotoxic substance. In one embodiment, the neuronal stem cell is genetically engineered using a viral vector encoding a therapeutic gene. In another embodiment the neuronal cell can be genetically engineered to express a suicide gene, a differentiating agent, or a receptor to any number of trophins. The neuronal cells if administered on the same side or a contralateral side of the brain from the tumor, are capable of reaching the tumor cells.

In another embodiment there is provided a method of converting a migrating neuronal cell to a migrating packaging/producer cell, said method includes the steps of a) providing a neuronal cell which constitutively produces a marker such as β-gal; b) cotransfecting the neuronal cell with an amphotropic pPAM3 packaging plasmid and a puromycin selection plasmid pPGKpuro; c) selecting transfected cells in puromycin; d) selecting for cell surface expression of the amphotropic envelope glycoprotein coat; e) isolating cells by fluorescent activated cell sorting using monoclonal antibody 83A25; and f) screening the cells of step e for their packaging ability by assessing which colonies packaged lacZ into infectious viral particles. Thus there is produced a migratory neuronal cell capable of being transfected with a gene of choice, so that viral particles expressing the gene of choice are produced and disseminated over a wide area of the central nervous system by a plurality of the transfected packaging cells.

The method of converting the migratory neuronal cell into a packaging cell line wherein step f. is performed by a virus focus assay for β-gal production. Alternatively the method can be performed with a prodrug activation enzyme as the gene of choice. Alternatively, the, prodrug activation enzyme is $E.\ coli$ cytosine deaminase (CD), HSV-TK or cytochrome p450. More preferably, the prodrug activation enzyme is $E.\ coli$ cytosine deaminase (CD).

Also disclosed is a novel cell packaging line for the central nervous system. The cell line includes neuronal cells which constitutively produce a marker such as 0-gal, have been cotransfected with an amphotropic pPAM3 packaging plasmid and a puromycin selection plasmid pPGKpuro; are selected in puromycin, for cell surface expression of the amphotropic envelope glycoprotein coat and for fluorescence using monoclonal antibody 83A25, and for their packaging ability by assessing which colonies packaged lacZ into infectious viral particles. The resulting cells are capable of packaging and releasing particles or vectors which, in turn, may serve as vectors for gene transfer to central nervous system cells. The particles in the novel cell packaging line can be replication-defective retroviral particles. The vectors in the novel cell packaging line can be replication-conditional herpes virus vectors.

The present invention is based upon a surprising finding that stem cells, more particularly neural stem cells, when administered intracranially can migrate throughout a tumor and track metastatic tumor cells to reach tumor cells in the brain. The invention provides a method for treating brain tumors by administering genetically engineered stem cells, more preferably neural stem cells in an individual affected with brain tumors. The invention also provides a method of preparing genetically engineered neural stem cells and a composition comprising the genetically engineered stem cells in a pharmaceutically acceptable carrier.

It is a further object of this invention to provide a safe, efficient and convenient system for delivering therapeutic agents to intracerebral tumors, cerebral metastases from an extracerebral tumor.

In one embodiment, the present invention provides a neuronal stem cell comprising a vector encoding a therapeutic agent. In one embodiment the vector is a replication conditional vector. In a preferred embodiment vector is a herpes simplex vector and in a most preferred embodiment the vector is a herpes simples type 1 vector. In a further preferred embodiment the herpes simplex type 1 vector is deficient for ribonucleotide reductase.

The invention also provides a method of treating a brain tumor in a mammal in need thereof, the method comprising a) providing a neuronal stem cell comprising a vector encoding a therapeutic agent; and b) administering said neuronal stem cell in a pharmaceutically acceptable carrier into a mammal in need thereof. In one embodiment, the method is used for treating a malignant glioma.

In one embodiment, replication of the vector is controlled by making the vector deficient for a component necessary for vector replication. In a preferred embodiment, the vector is made deficient for ribonucleotide reductase.

The invention also provides a method of treating a brain tumor in a mammal in need thereof the method comprising: a) providing a neuronal stem cell comprising a replication conditional vector encoding a therapeutic agent; b) inhibiting replication of said replication conditional vector in said neuronal stem cell; c) administering the neuronal stem cell of step b in a pharmaceutically acceptable carrier into a mammal in need thereof; and, d) enhancing replication of said replication conditional vector. In one embodiment, step b) is performed by inhibiting growth of the neuronal stem cell. In a preferred embodiment the growth inhibition is performed using mimosine. In a further embodiment, growth inhibition is performed using a combination of mimosine and ganciclovir.

The present invention further provides a method of treating a brain tumor in a mammal in need thereof said method comprising: a) administering into a mammal a neuronal stem cell comprising a herpes simplex type 1 vector encoding thymidine kinase; and b) administering ganciclovir into said mammal.

The invention also provides a method of preparing neural stem cells encoding a therapeutic agent, said method comprising: a) providing a neural stem cell; b) growing said neural stem cell to confluency; c) subjecting the neural stem cell to a replication-arresting protocol; d) infecting the replication arrested cell with RR-P450; and e) washing the infected cell, separating the cell from its growth surface and resuspending the cell in a medium to obtain a concentration of 50,000 cells/µl.

In a preferred embodiment, a method of preparing neural stem cells encoding a therapeutic agent comprises: a) providing a neural stem cell; b) growing said neural stem cell to confluency; c) subjecting the neural stem cell to a replication-arresting protocol, said protocol comprising treating cells with a medium comprising about 400 µM mimosine on days 0 and 4 and treating cells on day 6 with a medium comprising about 400 µM mimosine and optionally about 5 µM ganciclovir; d) infecting the replication arrested cell with RR-P450 at an MOI of 1 on day 7; and e) washing the infected cell, trypsinizing and resuspending in DMEM and optionally 5 µM GCV to obtain a concentration of 50,000 cells/µl.

BRIEF DESCRIPTION OF FIGURES

FIGS. 1A and 1B illustrate the migratory capacity of neural progenitor/stem C17.2 cells in vitro. After 5 days of incubation there was a wide distribution of C17.2 cells (FIG. 1B), suggesting that they had migrated far from their initial seeding in the cylinder, compared to TR-10 cells (FIG. 1A), which remained localized to the area of initial seeding in the cylinders. These patterns were observed whether the cells were plated directly on top of the glioma cells (right-sided cylinder arrows) or simply in juxtaposition to them (center cylinder arrows).

FIGS. 2A, 2B, 2C and 2D illustrate foreign gene-expressing neural progenitor/stem cells extensive migration throughout experimental tumor mass, and slightly beyond advancing tumor edge, appearing to "track" migrating tumor cells. (FIG. 2A) day 2 shown at 4X; arrowheads demarcate the approximate edges of tumor mass; (FIG. 2B) high power at 10× where X-gal, blue-staining NSCs (arrows) are interspersed between tumor cells staining dark red. (FIG. 2C) View of tumor mass 10 days after intratumoral injection showing X-gal-blue, C17.2 NSCs have infiltrated the tumor but largely stop at the edge of the darkly red stained tumor tissue with some migration into surrounding tissue when the blue-staining NSC appears to be "following" an invading, "escaping" cell (arrow)(10×). (FIG. 2D) CNS-1 tumor cells implanted into an adult nude mouse frontal cortex, there is extensive migration and distribution of blue C17.2 cells throughout the infiltrating experimental tumor bed, up to and along the infiltrating tumor edge (arrows), and where many tumor cells are invading normal tissue, into surrounding tissue in virtual juxtaposition to aggressive tumor cells (arrows)(10×).

(FIGS. 3C, 3D) low and high power of tumor edge and migrating tumor cell in juxtaposition to C17.2 cell (X-gal and neutral red); (FIGS. 3G, 3H) low and high power of single migrating tumor cells in juxtaposition to C17.2 cells (double immunofluorescent labeling with Texas Red and FITC).

(FIGS. 4A, 4B) same hemisphere: $3 \times 10^4$ CNS-1 tumor cells implanted into right frontal lobe. On day 6, $4 \times 10^4$ C17.2 cells injected into fight frontoparietal lobe (4 mm caudal tumor injection). Animals sacrificed on day 12 (shown) and day 21, C17.2 cells seen in tumor bed (X-gal and neutral red). (FIGS. 4C, 4D, 4E) Contralateral hemisphere: $3 \times 10^4$ CNS-1 tumor cells implanted into left frontal lobe and $5 \times 10^4$ CNS-1 tumor cells implanted into left frontoparietal lobe. On day 6, $8 \times 10^4$ C17.2 cells were injected into fight front lobe. Animals were sacrificed on day 12 and 21 (shown); c) $4 \times$C17.2 cells (red) seen migrating towards tumor (green) from opposite side of the brain, d) 10× C17.2 cells (red) seen actively migrating across central commisure (double immunofluorescence), e) 20×C17.2 cells (blue) seen entering tumor (black arrows)(X-gal/Neutral Red). FIGS. 4F, 4G show intraventricular $5 \times 10^4$ CNS-1 tumor cells were implanted into right frontal lobe. On day 6, $8 \times 10^4$ C17.2 cells were injected into right or left (shown) lateral ventricle.

DETAILED DESCRIPTION OF THE INVENTION

Figure 3A:
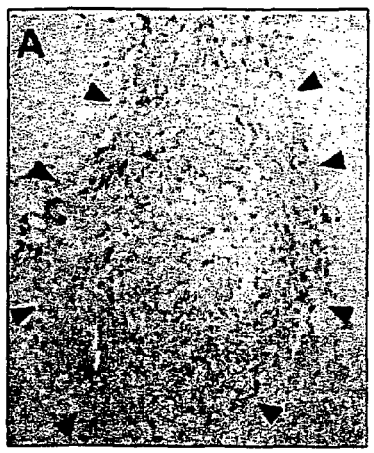
FIGS. 3A, 3B, 3C, 3D, 3E, 3F, 3G and 3H illustrate the neural progenitor/stem cel appearance to "track" migrating tumor cells away from main tumor mass, (FIGS. 3A, 3B) parallel sections: low power C17.2 cells distributed throughout tumor and surrounding edge (FIG. 3A) X-gal and neutral red, FIG. 3B) double immunofluorescent labeling with Texas Red and FITC.

The experiments presented herein demonstrate that NSCs (prototypical clone C17.2) when implanted into an experimental glioma, will distribute throughout the tumor and migrate along with aggressively advancing tumor cells, while continuing to express their reporter gene lacZ. (One of the glioma lines used, astrocytoma cell line CNS-1, demonstrates single cell infiltration and invasive characteristics similar to those of human glioblastomas"). Furthermore, the neural progenitor/stern cells seem to migrate slightly beyond and surround the invading tumor border. In additional experiments, where neural progenitors were implanted at a distant site from the tumor bed, in the same hemisphere, opposite hemisphere, or lateral ventricle, they migrated through normal tissue moving specifically toward CNS-1 tumor cells. They were found to accumulate in or near the tumor bed as well as near or in direct juxtaposition to the individual infiltrating tumor cells.

Not wishing to be bound by any particular theory, the inventors propose that this neural progenitor/stem cell system migrate towards a trophic gradient of growth factors produced by the tumor cells. Thus, NSCs may provide a unique platform for the dissemination of therapeutic genes to the proximity of or into tumors that previously were inaccessible. These observations further suggest a number of other new gene therapy approaches. These may include the dissemination of cytotoxic gene products, but could also include factors that directly promote differentiation of neoplastic cells as well as the more efficacious delivery of viral vectors encoding therapeutic genes to be incorporated by tumor cells (e.g. suicide genes, differentiating agents, receptors to trophins). Because NSCs can be engineered to package and release replication-defective retroviral particles or replication-conditional herpes virus vectors which, in turn, may serve as vectors for the transfer of genes to CNS cells, neural progenitor/stem cells should serve to magnify the efficacy of viral-mediated gene delivery to large regions in the brain.

One effective mode of therapy for experimental brain tumors has been prodrug activation. Initially, prodrug activation enzymes were limited to antibodies directed against tumor enriched antigens. New strategies incorporate genes for these enzymes into viral vectors. Among the prodrug activating systems shown to be effective for gliomas E. coli cytosine deaminase (CD), HSV-TK and cytochrome p450 have been demonstrated to have a drug mediated bystander effect. Of these CD gives the best reported "bystander" effect. CD converts the nontoxic prodrug 5-fluorocytosine (5-FC) to 5fluorouridine (5-FU) metabolites. 5-FU is a chemotherapeutic agent which has selective toxicity for actively dividing cells, thus primarily targeting tumor cells. In addition, 5-FU and its toxic metabolites can readily pass into adjacent and surrounding cells by nonfacilitated diffusion. Brain tumors may require only a small number of cells expressing CD (about 2% evenly distributed) to generate significant anti-tumor effects when treated with systemic, non-toxic levels of 5-FC. Our results support the hypothesis that transduced NSCs would disperse CD expression efficiently throughout the tumor and even "track" single migrating, "escaping" tumor cells.

Another approach to brain tumor gene therapy has been selective gene transfer to tumor cells in combination with pharmacotherapy, e.g., the HSV-TK gene, when transduced via retrovirus into a dividing population of brain tumor cells, confers a lethal sensitivity to the drug ganciclovir. Recent modifications of retroviral constructs to increase efficiency of infection and cell-specific targeting hold promise for enhancing the potency of this strategy. Again, through the "bystander" effect, tumor destruction is effective even when only a fraction of the cells express HSV-TK; adjacent tumor cells not expressing HSV-TK also appear to be eliminated. Attempts to improve efficiency of tumor destruction have focused on increasing the number of cells expressing the HSV-TK gene. The use of NSCs as packaging cells (which might then be self-eliminated) may prove to be an effective extended delivery system of the lethal gene to neighboring mitotic tumor cells, especially individual, infiltrating tumor cells.

In conclusion, genetically modified neural progenitor/stem cells have the potential to supply a range of tumor selective agents throughout mature and developing brains. The experiments presented here demonstrate the ability of NSCs: (1) to migrate/distribute quickly and effectively throughout the main tumor bed when implanted directly into the experimental gliomas; (2) to migrate slightly beyond and "surround" (as if to contain) the invading tumor border; (3) to seemingly "track" individual, infiltrating tumor cells into surrounding tissue; (4) to migrate through normal tissue from distant sites to target CNS-tumors; and (5) to show stable expression of a foreign gene, in this case lacZ, throughout the tumor bed and in juxtaposition to tumor cells. These results lay the groundwork for future therapeutic brain tumor studies, providing critical support for the use of neural progenitor/stem cells as an effective delivery vehicle for tumor directed, vector-mediated enzyme/prodrug gene therapy.

Other cells useful according to the invention include, but are not limited to the HCN-1 cell line which is derived from parental cell lines from the cortical tissue of a patients with unilateral megalencephaly growth [Ronnett G. V. et al., Science 248: 603-5, 1990]. HCN-1A cells have been induced to differentiate to a neuronal-like morphology and stain positively for neurofilament, neuron-specific enolase and p75NGFR, but not for myelin basic protein, S-100 or glial fibrillary acidic protein (GFAP). Because these cells also stain positively for 7-amino butyric acid and glutamate, they appear to become neuro-transmitting bodies. Earlier, it has been observed that HCN-I cells survived in the brain parenchyma and proposed that these cells may be suitable for intracerebral transplantation in humans [Poltorak et al., Cell Transplant 1: 3-15, 1992].

It has also been reported that HCN-1 cells grew processes resembling neurons when exposed to nerve growth factor, dibutyryl cyclic AMP and isobutylmethylxanthine [Ronnet et al., Neuroscience 63: 1081-99, 1994].

The nerve cells also can be administered with macrophages which have been activated by exposure to peripheral nerve cells. Such activated macrophages have been shown to clean up the site of CNS trauma, for example a severed optic nerve, after which new nerve extensions started to grow across the lesion. Implanting macrophages exposed to CNS tissue (which secretes a chemical to inhibit macrophages) or nothing at all resulted in little or no regeneration [Lazarov-Spiegler et al., FASEB J 10: 1, 1996].

Fetal pig cells have been implanted into patients with neurodegenerative diseases, such as Parkinson's disease and Huntington's chores, and intractable seizures, in whom surgical removal of the excited area would otherwise have been performed. Such cells, if properly screened for retroviruses, could also be used in the Inventive method.

Neural crest cells can be isolated and cultured, e.g. according to Stemple and Anderson (U.S. Pat. No. 5,654,183), which is incorporated herein by reference, with the modification that basic fibroblast growth factor (bFGF) is added to the medium at concentration ranging from 5-100 ng/ml in 5 ng/ml increments. Neural crest cells so cultured are found to be stimulated by the presence of FGF in increasing concentrations about 1 or 5 ng/ml. Such cells differentiate into peripheral nerve cells, which can be used in the instant invention.

The invention further provides a method for treating tumors by administering neural stem cell comprising a vector encoding a therapeutic agent in an individual affected by a brain tumor. The invention also provides a method of preparing the neural stem cells and a composition comprising the genetically engineered stem cells in a pharmaceutically acceptable carrier.

The genetically engineered neural stem cell based delivery method of the present invention offers a number of advantages over direct injection of virus into a tumor. For example, the virus can be activated after a delay to allow the cells to migrate towards metastatic tumor cells as described infra.

The neural stem cells useful according to the present invention include cells that are capable of migrating through a tumor, beyond a tumor/parenchyma border and brain tissue. These migrating stem cells can be prepared as described by Snyder [Snyder et al. Cell 68, 33-51, 1992; Snyder, The Neuroscientist 4, 408-25, 1998]. Other examples of migrating stem cells useful according to the present invention include, but are not limited to, neural stem cells, HSN-1 cells, fetal pig cells and neural crest cells, bone marrow derived neural stem cells, and hNT cells. The HSN-1 cells useful according to the invention can be prepared as described in, e.g., Ronnett et al. [Science 248, 603-605, 1990]. The preparation of neural crest cells in described in U.S. Pat. No. 5,654,183. The hNT cells useful according to the present invention can be prepared as described in, e.g, Konubu et al. [Cell Transplant 7, 549-558, 1998].

The stem cells according to the present invention are genetically engineered to deliver a therapeutic agent that can be used to substantially inhibit tumor cell growth. The term "inhibit" as used herein means inhibiting cell division and growth as well as causing necrotic or apoptotic cell death.

Such therapeutic agents include, but are not limited to vectors encoding genes for toxins; prodrugs; enzymes such as cytosine deaminase (CD); angiogenesis inhibitors such as TNP-470, platelet factor 4, thrombospondin-1, tissue inhibitors of metalloproteinases (TIMP1 and TIMP2), prolactin (16-kD fragment), angiostatin (38-kD fragment of plasminogen), endostatin, bFGF soluble receptor; cytokines; growth factors and their inhibitors; interleukins (IL), IL I-IL-2, IL-3, IL-4, IL-5, IL-6, IL-7, IL-8, IL-I0, and IL-I1; tissue necrosis factors (TNF) TNFα and TNFβ; lymphotoxin (LT); interferons (IFN) IFNα, IFNβ and IFNγ; tissue growth factors (TGF); colony-stimulating factors (CSFs); and nerve growth factor (NGF). In the preferred embodiment, the migrating stem cells are engineered to encode cytocine deaminase, which converts a non-toxic 5-fluorocytosine (5-FC) into a toxic 5-fluorouridine (5-FU).

For example, the examples infra show size reduction in the experimental tumor models in the CD/5-FC prodrug example, NSCs were able to express a bioactive transgene in vivo and to effect a significant anti-tumor result. 5-FU is a chemotherapeutic agent with selective toxicity to dividing cells through its toxic metabolites can readily diffuse into surrounding tumor cells giving CD an impressive "bystander" effect. As little as 2% of the tumor mass expressing CD can generate a significant antitumor effect in response to 5-FC [Huber et al., *Proc Natl Acad Sci USA* 91: 8302-8306, 1994].

Vectors useful according to the present invention include, but are not limited to (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picarnovirus vectors; (i) vaccinia virus vectors; and (j) a helper-dependent or gutless adenovirus. In a preferred embodiment the virus is a herpes simplex type 1 virus (HSV-1). In a most preferred embodiment, the vector is a replication-dependent HSV-1 vector which has been engineered to lack ribonucleotide reductase activity.

In delivery of HSV-1 vectors, it has to be kept in mind that cells which replicate HSV-1 will die in the process. Thus, for a cellular delivery system of HSV-1 vectors which relies on host cell migration prior to virus release, it is essential that viral replication is arrested to allow time for migration of infected cells. Ideally, an HSV-1 mutant would enter a "quiescent" state [Jamieson et al., *J Gen Virol* 76: 1417-31, 1995] in the carrier cell, and replication would be activated at a defined time. Since replication-conditional HSV-1 vectors do not propagate in non-dividing cells, the rationale used in these disclosed experiments was to suppress virus replication by arresting the growth of neural stem cell carrier cells prior to infection with a replication-conditional mutant virus. The plant non-protein amino acid, mimosine, found in *Leucaena* and *Mimosa* genera [Hylin, *Biochem Pharmacol* 14: 1167-9, 1969], was used to arrest progression through the cell cycle from G1 to S-phase [Mosca et al., *Mol Cell Biol* 12: 4375-83, 1992] and to inhibit cellular and viral ribonucleotide reductase (RR) activity by chelating iron, which is essential for RR function [Dai et al., *Virology* 205: 210-6, 1994].

Mimosine treatment suppresses replication of HSV-1 virus deficient for RR both by decreasing cellular RR activity through growth arrest of the host cells and direct inhibition of activity. Since the effects of mimosine are reversible, removal of mimosine should allow the cells to commence growth and restore the function of cellular RR, thus becoming permissive for replication of the mutant virus.

As an additional guarantee that virus replication is completely abrogated upon infection, growth-arrested neural stem cells can also be treated with ganciclovir (GCV). GCV acts as a false nucleoside and inhibits viral DNA synthesis in HSV-1 infected cells. GCV or other substrates of HSV-TK have been used in cellular models of HSV-1 latency virus in neuronal cells [Wigdahl et al., *J Virol* 49, 205-14, 1984; Wilcox and Johnson, *J Virol* 61, 2311-5, 1987], and hence may promote a similar benign, quiescent state in neural progenitor cells. Thus in the present model, the mutant virus infecting growth-arrested neural stem cells should enter a quiescent state, and any residual replication will be blocked by GCV. In this scenario, it is important to know whether the quiescent HSV-1 genomes can be reactivated into a replicating state after an extended period. Studies in culture models of HSV-1 latency in neuronal cells have shown that treatment with glucocorticoids [Halford et al., *J Virol* 70, 5051-60, 1996; Hardwicke and Schaffer, *J Virol* 71, 3580-7, 1997] or NGF-deprivation [Wilcox and Johnson, *J Virol* 61, 2311-5, 1987] can trigger reactivation. Several HSV-1 proteins, e.g. infected-cell protein (ICP)4 [Kramer and Coen, *J Virol* 71, 5878-84, 1997], ICPO [Zhu et al., *J Virol* 64, 4489-98, 1990], VP16 [Sears et al., *J Virol* 65, 2929-35, 1991], TK [Jacobson et al., *J Virol* 67, 5383-93, 1993; Wilcox et al., *Virology* 187, 348-52, 1992] and RR [Chang et al., *Virology* 185, 437-40, 1991], have all been implicated in the reactivation process of HSV-1 in neuronal cells.

The stem cells can also be engineered to controllably express the therapeutic agent. Such controlled expression systems include, but are not limited to drug/hormone inducible promoters, e.g., tetracycline [Gossen and Bujard, *Nucl Acids Res* 21, 4411-2, 1993], rapamycin [Rivera et al., *Nat Med* 2, 1028-32, 1996], and glucocorticoid inducible promoters [Lu and Federoff, *Hum Gene Ther* 6, 419-28, 1995]; tetracycline silencer system [Freundlieb et al., *J Gene Med.* 1, 4-12, 1999], particularly combined with a "piggyback" HSV-1 delivery system [Pechan et al., *Hum Gene Ther* 7, 2003-13,1996].

In the preferred embodiment, a replication-dependent HSV-1 vector is produced by deleting the ribonucleotide reductase (RR) gene of HSV-1 vector to render the vector susceptible to control by external expression of RR.

To avoid destruction of delivery cells by viral replication upon implantation, regulation of expression of genes by viral vectors is desired. Delayed expression allows better migration of the cells infected with a viral vector. It is preferred that the expression can be delayed for 1-6 days, preferably 3 days after the injection of the cells to avoid self-destruction of the delivery cells and to allow the migrating stem cells to reach potential metastatic tumor cells. When using the inducible systems in viral vectors, it is important to achieve full-off baseline expression to prevent residual viral replication which can result in premature death of migrating stem cells infected with the In one embodiment, the present invention provides migrating neural stem cells infected with an HSV-1 vector which has been engineered to lack the RR enzyme thereby rendering it non-replicable in the absence of externally produced RR. Because the HSV-1 vector can only replicate in dividing cells, virus replication can be regulated by regulating cell division.

Control of replication-conditional HSV-1 vector lacking RR can be achieved, for example, by arresting the carrier cell, i.e. the neural stem cell growth prior to infection. For example, the drug mimosine can be used to block growth of neural stem cells at confluency and thus prevent virus replication. In addition to arresting the cell cycle in the late G1 phase, mimosine also inhibits cellular RR enzyme. Addition of mimosine on infected cells in vivo completely abolishes viral replication which is resumed after removal of mimosine. The mimosine block of cell division and viral replication is reversible at treatment times at least up to 13 days.

In another embodiment, co-treatment with ganciclovir (GCV) and mimosine as a viral replication block can be used. After GCV treatment, neural stem cells differentiate into neurons and harbor the virus in a latent state. After withdrawal of GCV and mimosine the cells need a high level of RR to allow the re-entry of the quiescent viral genome of the replication-conditional HSV-1 RR⁻ onto the replicative cycle. Alternatively, the immediate early virus proteins ICPO or ICP4 that are known to be important in the HSV-1 re-activation can be used to re-activate the arrested viral replication [Zhu et al., *J Virol* 64, 4489-98, 1990]. In addition, viral replication proteins like ICP4 and CIP27 can also be placed under control of drug/hormone inducible promoters.

Additional genes can be inserted into the replication-dependent vector. A non-limiting example is CYP2B 1 gene, which is responsible for the bio-activation of prodrugs cyclophosphamide and ifosfamide. Once the packaging cells have migrated to the appropriate site, the appropriate prodrug can be administered to produce an oncolytic effect. Similarly, not all the components of the tested vector are believed to be necessary. Vector constructs may additionally include a marker gene for potential histological tracking. Such markers include, but are not limited to lacZ or genes encoding fluorescent proteins such as green fluorescent protein, GFP.

The migrating stem cells according to the present invention can be administered to an individual in a pharmaceutically acceptable carrier intracranially, e.g., at the time of surgical removal of the tumor.

The practice of the present invention will employ, unless otherwise indicated, conventional techniques of cell biology, cell culture, molecular biology, transgenic biology, microbiology, recombinant DNA and immunology, which are within the skill of the art. Such techniques are described in the literature. [See, for example, MOLECULAR CLONING: A LABORATORY MANUAL, 2d ed. Ed. by Sambrook Fritsch and Maniatis Cold Spring Harbor Laboratory Press. 1989; DNA CLONING: VOLUMES I AND II. Ed. by D. N. Glover, 1985; OLIGONUCLEOTIDE SYNTHESIS. Ed. by M. J. Gait, 1984; Mullis et al., U.S. Pat. No. 4,683,195; NUCLEIC ACID HYBRIDIZATION. Ed. by B. D. Hames and S. J. Higgins, 1984; TRANSCRIPTION AND TRANSLATION. Ed. by B. D. Hames and S. J. Higgins, 1984; CULTURE OF ANIMAL CELLS Ed. by R. I. Freshney, Alan R. Liss, Inc., 1987; IMMOBILIZED CELLS AND ENZYMES, IRL Press, 1986; PRACTICAL GUIDE TO MOLECULAR CLONING, B. Perbal, 1984; GENE TRANSFER VECTORS FOR MAMMALIAN CELLS, Ed by J. H. Miller and M. P. Calos, Cold Spring Harbor Laboratory, 1987; METHODS IN ENZYMOLOGY: VOLS. 154 AND 155, Ed. by Wu et al.; IMMUNNOCHEMICAL METHODS IN CELL AND MOLECULAR BIOLOGY, Ed. by Mayer and Walker, Academic Press, London, 1987; HANDBOOK OF EXPERIMENTAL IMMUNOLOGY: VOLS. I-IV, Ed. by D. M. Weir and C. C. Blackwell, 1986; MANIPULATING THE MOUSE EMBRYO, Cold Spring Harbor Laboratory Press, Cold Spring Harbor, N.Y., 1986].

The references cited throughout the specification are herein incorporated in their entirety. The present invention is further illustrated by the following examples and claims. The following examples are provided to aid in the understanding of the invention and are not to be construed as a limitation thereof.

EXAMPLES

Materials and Methods

Cells

Neural crest cells were isolated and cultured according to Stemple and Anderson [U.S. Pat. No. 5,654,183], which is incorporated herein by reference. With the approximately 60-70% confluency around a 5 mm cylinder (i.e. free of CNS-1 cells) into which 40,000 C17.2 or TR-10 cells were plated overnight. At the same time, 40,000 C17.2 or TR-10 cells were placed into a 5 mm cylinder placed directly on top of adhered CNS-1 cells. The next day, cylinders were removed and plates rinsed well with PBS to remove any floating cells, media was replaced, and plates incubated for 5 days. Plates were subsequently stained for β-galactoside overnight after. 5% glutaraldehyde fixation. (Note: both C17.2 and TR-10 cells were>90% blue with X-gal staining).

The neural stem cells (NSCs) were from a stable, well established, well studied, prototypical multipotent engraftable murine neural stem cell clone transfected with and constitutively expressing the lacZ marker gene (clone C17.2) [Snyder et al., *Cell* 68: 33-51, 1992; Snyder et al., *Nature* 374: 367-70, 1995; Snyder et al., *Proc Natl Acad Sci USA* 94: 11663-68, 1997]. Described and characterized extensively elsewhere [Snyder, *The Neuroscientist* 4: 408-25, 1998], this clone of neural stem cells has been shown to be an effective vehicle for gene transfer to the CNS [Snyder et al., *Nature* 374: 367-70, 1995; Lacorraza et at., *Nature Med* 4: 424-29, 1996]. Prototypical human NSC clones H1 and H6 also were used [Flax et at., *Nat Biotechnol* 16: 1033-39,1998].

NSCs were transduced with cytosine deaminase. A plasmid using the retroviral pBabePuro backbone [Morgenstern and Land, *Nucl Acids Res* 18: 3 5 87-96, 1990] was constructed to include the *E. coli* cytosine deaminase cDNA (1.5 kb fragment) under the LTR promoter (kindly provided by Dr. Michael Black). Retrovirus vectors were packaged by co-transduction of the Cdpuro plasmid with amphotropic (MI2YA) or ecotropic (MV 12) envelope-coding plasmid CDNA [Sena-Estees et at, *J* 15 *Virol* 73: 10426-39, 1999] into 293T/17 cells [Pear et at, *Proc Natl Acad Sci USA* 90: 8392-96, 1993].

Cdpuro retroviral supernatant was harvested as previously described [Sena-Esteves et al., *J Virol* 73: 10426-39, 1999] and used for multiple infections of several lacZ-positive NSC clonal lines (human HI, H6 and murine C17.2). Transduced NSC populations were placed under puromycin selection for at least two weeks.

The CHS-1 rat glioma cell line was generated from a glioma induced in a Lewis rat by treatment with N-nitroso-N-methylurea [Kruse et at, *J Neuro-Oncology* 22: 191-200, 1994] and was obtained from Drs. C. A. Kruse and W. F. Hickey (University of Colorado Health Sciences Center, Denver, Colo.). The CNS-1 cells were engineered via retroviral-mediated gene transduction to constitutively express GFP as previously described [Short et al., *J Neurosci Res* 27: 427-39, 1990] CHS-1 cells were maintained in RPMI-1640 (BioWhitaker) supplemented with 10% fetal calf serum (FCS) at 370 C in a standard 5% $CO_2$ incubator at 100% humidity.

In vivo studies: 48 hours prior to transplant, C17.2 and TR-10 cells were incubated with BUdR (Sigma) at a concentration of 10 μM. Plated cells were rinsed with PBS, trypsinized, resuspended in media and counted on the Coulter counter. Desired number of cells were spun down at 4° C. in the centrifuge for 4 minutes and 1100 rpm to obtain a pellet. Media was removed; cells were rinsed by resuspending in PBS and respun. PBS was removed and the appropriate amount of PBS added to resuspend cells at final desired concentration. Cells were kept on ice, and gently triturated prior to each animal injection. Cells not labeled with BUdR were prepared for injection in similar manner.

Animals: Animal studies were performed in accordance with guidelines issued by the Massachusetts General Hospital Subcommittee on Animal Care. Animals used: adult CD-Fisher rats (Charles River) and 8-10 week old adult, approximately 20 gram female nude mice (random bred Swiss white obtained from Cox 7, MGH-East).

Animals were anesthetized by an i.p. injection of 15 ml of 20% ketamine HCL (KETALAR 100 mg/ml; Parke-Davis, Morris Plains, N.J.), 20% xylazine (ROMPLTN 20 mg/ml; Miles Inc., Shawnee Mission, Kans.), 60% sodium chloride (0.9%; Abbott Laboratories, North Chicago, Ill.) and immobilized in stereotactic apparatus (Kopf, Tujunga, Calif.). Intracerebral injections were stereotactically performed by making a linear scalpel skin incision on top of the skull. A burr hole was drilled into the skull with a high speed drill 2 mm lateral to the bregma on the coronal suture. After incising the dura with a sterile needle and obtaining hemostasis, desired number on tumor cells suspended in 1 μl of 1× Dulbecco's phosphate-buffered salt solution (PBS pH 7.4; Mediatech, Herndon, Va.) were injected with a 26 gauge 5 μl Hamilton syringe to specified location (see protocols below) over a 3 to 5 minute period. After retracting the needle over a 2-4 minute period, bone-wax (Ethicon, Somerville, N.J.) was used to occlude the burr hole, betadine applied to surgical area, and the skin sutured closed. Animals receiving a second injection at a later date were anesthetized, immobilized in stereotactic apparatus, and cells injected as per specific protocol (see below). Animals were sacrificed on stated days with an overdose of anesthesia and subsequent intracardiac perfusion with PBS followed by 4% pamfonnaldehyde and 2 mM $MgCl_2$ (pH 7.4). Brains were removed and post-fixed overnight at 4° C. and then transferred to 30% sucrose in PBS and 2 mM $MgCl_2$ (pH 7.4) for 3-7 days to cryoprotect. Brains were stored at −80° C. and then 10-15 micron coronal serial sections were cut to cryostat (Leica CM 3000).

BUdR Labeling of Engrafted C17.2 Cells

Selected animals received 3 intraperitoneal injections of 1 ml/100 g body weight 20 μM BUDR stock solution (Sigma) over 24 hours prior to sacrifice (0.2 ml/injection per 20 g mouse).

Histopathological and Immunohistochemical Studies

Tissue sections were stained with (1) X-gal and counterstained with neutral red (2) hematoxylin and eosin (3), double immunofluorescent labeling was performed with Texas Red anti-beta-galactosidase and FITC anti-GFP. Slides were examined with light microscopy, fluorescent microscopy. CNS-I tumor cells were also examined without staining under confocal fluorescent microscopy.

For histological analysis, animals were euthanized on the days specified below by deep anesthesia with at least 500 μl ketamine/xylazine solution intraperitoneally (i.p.) and subsequent perfusion with a 4% paraformaldehyde solution in PBS (4% PFA). The brain was removed and post-fixed in 4% PFA and 2 mM MgCl2 (pH 7.4) for 2 days, cryo-protected in 30% sucrose in PBS, and frozen at −80° C. Brains were sectioned at 10-15 μm using a cryostat and stained with neutral red. For lacZ-encoded β-galactosidase staining, mounted slices were placed at 37° C. in X-gal staining solution containing 5 mM potassium ferrocyanide, 5 mM potassium ferricyanide, 2 mM magnesium chloride, 1 mg/ml X-gal (Fisher, Pittsburgh, Pa.), and 2.5% di-methyl-sulfoxide (Sigma, St. Louis, Mo.) in PBS [Turner et al., Stain Technol 65: 55-67, 1990]. The sections were washed with PBS and counterstained with hematoxylin.

Cell Lines and Replication-conditional HSV-1 Mutants

The mutant HSV-1 vector, hrR3, was obtained from Dr. S. K. Weller (University of Connecticut Medical School) [Goldstein and Weller, *J Virol* 62: 2970-7, 1988]. It has an insertion of the *E. coli* lacZ gene into the UL39 locus coding for the large subunit of ribonucleotide reductase/infected cell protein ICP6. LacZ expression is under control of the ICP6 early virus promoter. Vector RR-P450, with an insertion of the cytochrome P450 gene into the lacZ locus of the hrR3 virus, was provided by Dr. E. A. Chiocca (Massachusetts General Hospital, Boston, Mass.).

HSV-1 vectors were grown on Vero cells (African green monkey kidney cells, ATCC #CCC81). Eighty to 90% confluent monolayers in 175 cm flasks were infected at an MOI of 1 pfu/cell. At the time of maximal cytopathic effect (~36-48 h after infection), cells and supernatants were harvested using a cell scraper. Cells were lysed by 3 cycles of freezing and thawing, cell debris was spun down at 700 g for 10 min, and virus stocks were stored at −80° C. Virus titers were determined by standard plaque assays [Roizman and Spear, *J Virol* 2, 83-84. 1968]. Virus stocks, typically $10^{10}$ plaque forming units (pfu)/ml, were thawed immediately prior to use. Procedures involving virus were performed in accordance with the guidelines issued by the Harvard Office of Biological Safety.

The neural stem cells employed were derived from a stable, well established, well studied, prototypical multipotent engraftable murine neural stem cell clone transfected with and constitutively expressing the lacZ marker gene (clone C17.2) [Snyder et al., Cell 68: 33-51, 1992; Snyder and Macklis, Clin Neurosci 3: 310-16, 1996]. Described and characterized extensively elsewhere [Snyder, The Neuroscientist 4: 408-25, 1998], this clone of neural stem cells has been shown to be an effective vehicle for gene transfer to the CNS [Snyder et al., Nature 374: 367-70, 1995; Lacorraza et al., Nature Med 4: 424-29, 1996]. The CNS-1 rat glioma cell line was generated from a glioma induced in a Lewis rat by treatment with N-nitroso-N-methylurea [Kruse et al., J Neuro-Oncology 22: 191-200, 1994] and was obtained from Drs. C. A. Kruse and W. F. Hickey (University of Colorado Health Sciences Center, Denver, Colo.). CNS-1 cells were grown as monolayers in Dulbecco's modified Eagle's medium (DMEM) supplemented with 10% fetal calf serum (FCS), 100 U/ml penicillin, and 100 μg/ml streptomycin (Gibco, Gaithersburg, Md.) at 37° C. in 5% carbon dioxide.

HSV-1 Amplicon Vectors

A series of amplicon plasmids were used to generate amplicon vectors: pHSV16, PHSVRR, and pHSVlacZ. To construct PHSV 16, a 1.9 kb fragment containing the coding sequence of VP 16 was cut out from PNFT (ATCC#68668) with PstI and HindIII ligated into pHSVPrPUC (kindly provided by Dr. H. Federoff, University of Rochester, Rochester, N.Y.) after digestion with BamHI and partial digestion with PstI. In this plasmid, VP 16 is driven by the HSV IE4/5 promoter. pHSVRR, expressing RR from an IE 4/5 promoter, was constructed by inserting a EcoR VlXtXhoI (partial digest) 4.8 kB fragment from pKHF (kindly provided by Dr. S. Weller, University of Connecticut) containing the coding sequence for both the long subunit (UL39) and the short subunit (UL40) of ICP6/RR into the SalIIBamHI (blunted) sites of the potylinker site of the pHSVPrPUC. pHSViacZ expresses lacZ under the control of the IE4/5 promoter [Geller and Breakefield, *Science* 241, 1667-9, 1988].

Helper virus-free stocks of HSVRR, HSV 16, and HSVIacZ amplicons were generated according to the method developed by Fraefel et al. [J Virol 70, 7190-7, 1996]. A set of 5 overlapping cosmids, which cover the whole HSV-1 genome [Cunningham and Davison, Virologv 197, 116-24, 1993] and are deleted at their packaging signals, were kindly provided by Dr. C. Fraefel (Massachusetts General Hospital, Boston, Mass.). 106 Vero 2-2 cells [Smith et al., 1992] were plated in p60 dishes and transfected with 0.6 μg plasmid DNA, as well as 0.2 μg DNA each of the 5 cosmids using LipofectAMINE (Gibco BRL, Life Technologies, Rockville, Md.). Using this method, only amplicon DNA is packaged into virions, as only this DNA contains a packaging signal. On day 3 after transfection, amplicon stocks were harvested by scraping the cells, three cycles of freezing and thawing, and sonication for 16 sec. Helper-free amplicon stocks were checked for the presence of wild type virus by infecting 100,000 Vero cells per well in a 24-well plate with 500 41 amplicon stock per well and then observing for cytopathic effect. No amplicon stocks contained detectable wild type virus by this assay. HSV-IacZ amplicon stocks were titered on confluent Vero cells by staining for P-galactosidase 16 h after infection for 4 hours at 37° C. in the X-gal staining solution containing 5 mM potassium ferrocyanide, 5 mM potassium ferricyanide, 2 mM magnesium chloride, 1 mg/ml X-gal (Fisher, Pittsburgh, Pa.) and 2.5% di-methyl-sulfoxide (Sigma, St. Louis, Mo.) in PBS [Turner et al., Stain Technol 65, 55-67, 1990].

Treatment of Neural Stem Cells with Mimosine and GCV, and Infection Treated Neural Stem Cells with HSV-1 Mutants Neural stem cells were grown in 24-well plates until they reached confluency (approximately 400,000 cells/well). Medium was changed every third day. Starting at confluency, day 0, some wells were treated with 400 μM mimosine (Sigma, St. Louis, Mo.). Medium was replaced on day 4 and day 6. On day 6, some mimosine-pretreated wells were additionally treated with 5 μM GCV (GCV, Cytovene-IV, Hoffmann La Roche, Nutley, N.J.). Cell culture medium was changed again on days 10, 13 and 17. On days 10 and 13 some previously mimosine ±GCV wells were washed 3 times with Hanks balanced medium (HBSS) and put back into growth medium. In addition, some mimosine ±GCV wells were washed, trypsinized, and split 1:8. Cell morphology and cells/well for different treatment conditions were determined in duplicate on days 0, 4, 7, 10, 13, and 17. The number of cells/well was determined using a Coulter Counter (Coulter Electronics, Hialeah, Fla.).

To determine the effects of mimosine and GCV treatment on replication of RR-HSV-1 mutants hrR3 and RRP450 in neural stem cells, cells were counted in duplicate on day 7 of treatment and infected at an MOI of 1 or 10. Virus titers in the conditioned medium—and in some experiments also in cell lysates—were determined by standard plaque tests on Vero cells. Virus titers and nwnbers of viable cells were determined on days 10, 13, and 17 after the start of mimosine treatment. Also, the influence of the expression of viral proteins VP 16 and ICP6 (RR), mediated by infection with amplicon vectors, on the replication of hrR3 mutant virus was determined at different time points after infection of neural stem cells. Stocks of helper-free packaged amplicons HSV 16. HSVRR and HSVIacZ (100 μl each) were added to the wells on day 7, 10, or 13. Three days later titers of hrR3 in the medium were determined by plaque assay.

In Vivo Experiments and Histological Analysis

Intracerebral injection of CHS-1 tumor cells was carried out as follows: Female 8-10-week-old nude mice (randomly bred Swiss-White were anesthetized by intraperitoneal (i.p.) injection with 70 μl of a solution consisting of 2 parts bacteriostatic 0.9% NaCl (Abbott, Ill.), and 1 part each of 20 mg/ml xylazine (Rompun™, Miles, Kans.) and 100 mg/ml ketamine (Ketalar™, Parke-Davis, N.J.). After positioning the animals in a stereotactic apparatus (Kopf, Tujunga, Calif.), a midline skin incision was made, and a burr hole was drilled~2 mm lateral and I mm anterior to bregma. Cells were injected into the forebrain over a period of 3-5 min to a depth of 2-4 mm from the dura using a Hamilton syringe. The needle was gradually retracted over 3-5 min, the burr hole was closed with bone wax (Ethicon). and the wound was washed with Betadine antiseptic (Purdue Frederick, Norwalk, Conn.). For secondary injections the same procedure was repeated.

For in vivo experiments, neural stem cells were grown to confluency in 6-well plates. Treatment with 400 μM mimosine was started on day 0, and medium was changed on days 4 and 7. On day 6, 5 μM GCV was added to some wells. On day 7, the cells per well were counted, and remaining wells were infected with RR-P450 at an MOI of 1. On day 10, the medium and cell lysates of infected neural stem cells were assayed in a plaque test; and the remaining wells were washed 3 times, trypsinized, counted, and resuspended in DMEM, or DMEM +5 μM GCV, at a concentration of 50,000 cells/)il. Two μl aliquots of this cell suspension were injected into intracerebral gliomas in nude mice. The gliomas were produced by implanting 5 days earlier an injection of 200,000 CNS-1 cells into the right frontal lobe. Also, in one experiment, 2 mice each were injected with $10^4$ or $10^5$ pfu RRP450 in 2 μl DMEM directly into the frontal lobe tumor.

Intracerebral injection of CNS-1 tumor cells, virus and neural stem cells were carried out as follows: male 6-8 weeks old nu/nu nude mice (obtained from the MGH Facility/Edwin Steele Laboratory) were anesthetized by intraperitoneal (i.p.) injection with 70 μl of a solution consisting of 2 parts bacteriostatic 0.9% NaCl (Abbott, Ill.), and 1 part each of 20 mg/ml xylazine (Rompun, Miles, K A) and 100 mg/ml ketamine (Ketalar™, Parke-Davis, N.J.). After positioning the animals in a stereotactic apparatus (Kopf, Tujunga, Calif.), a midline skin incision was made, and a burr hole was drilled 2 mm rostral and 2 mm right of bregma. Cells were injected over a period of at least 2 min to a depth of 2.5 mm from the dura using a Hamilton syringe. The needle was gradually retracted over 2 min, the burr hole was closed with bone wax (Ethicon), and the wound was washed with Betadine (Purdue Frederick, Norwalk, Conn.). For secondary injections the same procedure was repeated.

For histological analysis, animals were euthanized on day 13 (3 days after intracranial injection of virus-infected neural stem cells, virus or vehicle) by deep anesthesia with at least 500 pl ketamine/xylazine solution i.p. and subsequent perfusion with a 4% paraformaldehyde solution in PBS (4% PFA). The brain was removed and post-fixed in 4% PFA for 2 days, cryo-protected in 30% sucrose in PBS, and frozen at −80° C. Brains were sectioned at 12 μM using a cryostat and stained with neutral red. For lacZ-encoded β-galactosidase staining, mounted slices were placed for 24 hours at 37° C. in X-gal staining solution containing 5 mM potassium ferrocyanide, 5 mM potassium ferricyanide, 2 mM magnesium chloride, 1 mg/ml X-gal (Fisher, Pittsburgh, Pa.), and 2.5% di-methylsulfoxide (Sigma, St. Louis, Mo.) in PBS (Turner et al., 1990, ibid). The sections were washed with PBS and counterstained with hematoxylin. Immunohistochemistry was performed using standard biotin-avidin-bound peroxidase techniques (Vectastain ABC kit, Vector, Burlingame, Calif.) and a primary antibody against HSV-TK (rabbit polyclonal, dilution 1:500, gift of Dr. W. Summers, Yale University School of Medicine, New Haven, Conn.). Methylgreen was used as a counterstain. Some sections were double-stained for β-galactosidase and HSV-TK. In those cases, β-galactosidase staining was performed first, followed by HSV-TK immunohistochemistry and hematoxylin counterstaining.

Example 1

Migratory Capacity of NSCs in Culture

To determine properties of the NSCs in association with glioma cells, studies were initially performed in culture comparing the relative migratory capacity of NS-, (clone C17.2) to fibroblasts (the lacZ-expressing TR-10 fibroblast cell line) when cocultured with glioma cells. C17.2 and TR-10 cells were maintained in Dulbecco's modified Eagle's medium (DMEM; Mediatech, Washington, D.C.) supplemented with I 0% fetal calf serum (FCS; Sigma, St. Louise, Mo.), 5% horse serum (HS;Gibco), 1% Glutamine (2 mM; Gibco), 1% penicillin/streptomycin (Sigma). CNS-1 cells were stably transduced with the PGK-GFP-IRES-NeoR retroviral vector construct to express green fluorescent protein (GFP) as previously described [Aboody-Guterman et. al, 1997], and maintained in RPNH-1640 (Bio Whittaker) supplemented with 10% FCS and 1% penicillin/streptomycin (Sigrna). Cell structure studies were performed in 100 mm petri dishes under standard conditions: humidified, 37° C., 5% C02 incubator. CNS-1 glioma cells were plated to approx. 60-70% confluency around a 5 mm cylinder (i.e. free of CNS-1 cells) into which 40,000 C17.2 or TR-10 cells plated overnight. At the same time, 40,000 C17.2 or TR-10 cells were placed into a 5 mm cylinder placed directly on top of adhered CNS-1 cells. The next day, the cylinders were removed and plates rinsed well with PBS to remove any floating cells, media was replaced, and plates incubated for 5 days. Plates were subsequently stained for 0-galactosidase overnight after 5% glutaraldehyde fixation. (Note: both C17.2 and TR-10 cells are >90% blue with X-gal staining).

There was a wide distribution of C17.2 cells (FIG. 1B), suggesting that they had migrated far from their initial sites in the cylinder, compared to the TR-10 cells (FIG. 1A), which remained localized to the area of initial seeding in the cylinders. These patterns were observed whether the cells were plated directly on top of the glioma cells (rightsided cylinder arrows) or simply in juxtaposition to them (center cylinder arrows).

Example 2

Transgene-Expressing NSCs Migrate throughout and Beyond Invading Tumor Mass In Vivo To determine the behavior of clone C17.2 NSCs introduced into brain tumors, experimental animals (syngeneic adult rats) first received an implant of $4 \times 10^4$ D74 rat glioma cells in 1 μl injected into the right frontal lobe. Four days later, $1 \times 10^5$ C17.2 NSCs in 1.5 μl PBS were injected at same coordinates directly into the D74 tumor bed. Animals were then sacrificed at days 2, 6, and 10 days post-intratumoral injection and cryostat sections of the brains were processed with X-gal histochemistry for P-galactosidase (β-gal) activity to detect donor-derived cells and counterstained with neutral red to detect tumor cells. Donor C 1 7.2 NSCs were found extensively dispersed throughout the tumor within a few days, spanning an 8 mm width of tumor as rapidly as 2 days after injection (FIGS. 2A, 2B). This is a much more extensive and rapid dispersion compared to previous reports of 3T3 fibroblasts grafted into an experimental brain tumor [Rainov et al., Cancer Gene Ther 3: 99-106, 1996]. By day 10, C17.2 cells were seen throughout a majority of the tumor, clearly along the infiltrating tumor edge and slightly beyond it, drawn somewhat by the degenerative environment, seeming to "track" migrating tumor cells (FIGS. 2C, 2D). C17.2 cells themselves did not become tumorigenic. (FIG. 2A) Day 2 shown at 4X; arrowheads demarcate the approximate edges of tumor mass; even at lower power, the tumor can be seen to be intermixed with blue NSCs [arrows]. This is appreciated more dramatically at high power in (FIG. 2B) at 10× where X-gal+, blue-staining NSCs (arrow) are interspersed between tumor cells staining dark red. (FIG. 2C) This view of the tumor mass, 10 days after intra-tumoral injection nicely shows that X-gal+blue, C17.2 NSCs have infiltrated the tumor but largely stop at the edge of the darkly red stained tumor tissue (border indicated by arrowheads) with some migration into surrounding tissue when blue-staining NSC appears to be "following" and invading, "escaping" tumor cell (arrow) 10X. This phenomenon becomes even more dramatic when examining the behavior of C17.2 NSCs in an even more virulent, invasive and aggressive tumor than D74, the experimental CNS-I astrocytoma in the brain of a nude mouse (FIG. 2D). CNS-1 tumor cells were implanted into an adult nude mouse frontal cortex (day 0). On day 6, $4 \times 10^4$ C17.2 cells were implanted directly into the tumor bed. The animal pictured in (FIG. 2D) was sacrificed on day 12 post-tumor implantation, 6 days post-intra-tumoral injection. The cryostat section pictured was processed with X-gal histochemistry for β-galactosidase activity to detect blue C17.2 NSCs and counterstained with neutral red to show dark red tumor cells. There is extensive migration and distribution of blue C17.2 cells throughout the infiltrating experimental tumor bed, up to and along the infiltrating tumor edge (white arrows), and, where many tumor cells are invading normal tissue, into surrounding tissue in virtual juxtaposition to aggressive tumor cells (arrows) (10×).

Example 3

NSCs "Track" Infiltrating Tumor Cells

Figure 3B:
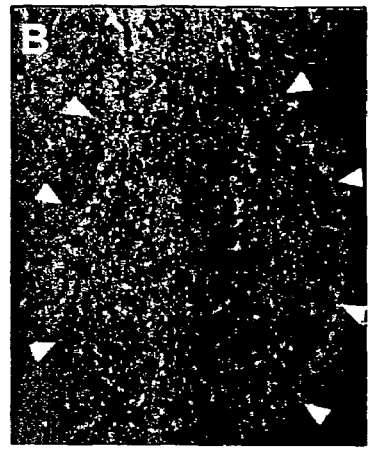
Figure 3C:
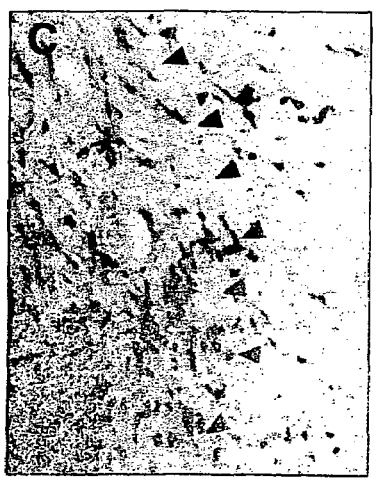
Figure 3D:
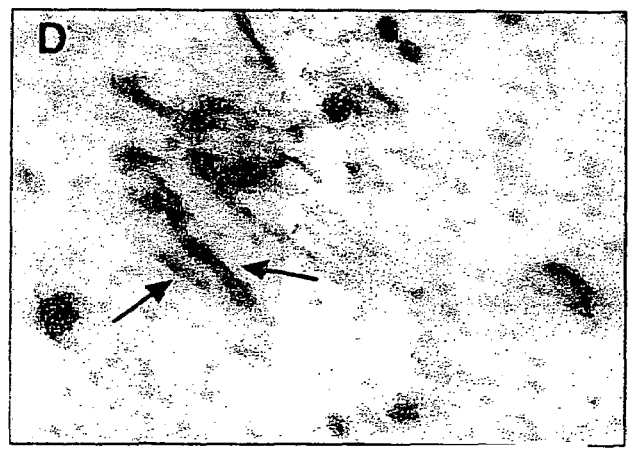
Figure 3E:
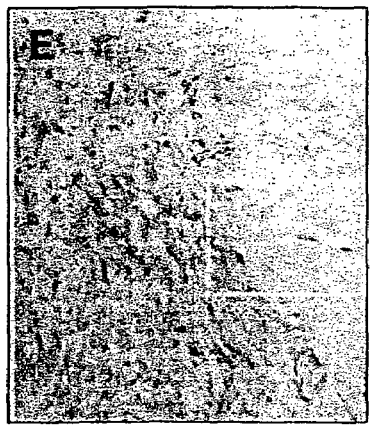
Figure 3F:
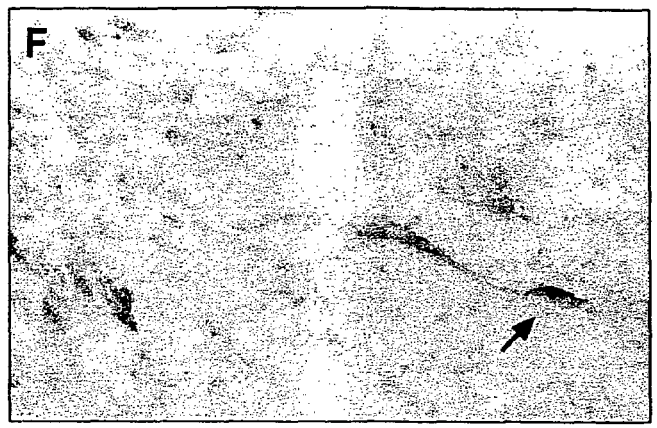
Figure 3G:
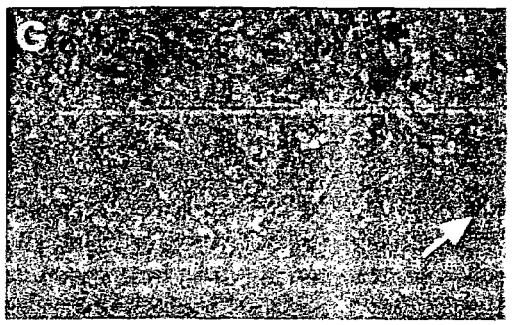
Figure 3H:
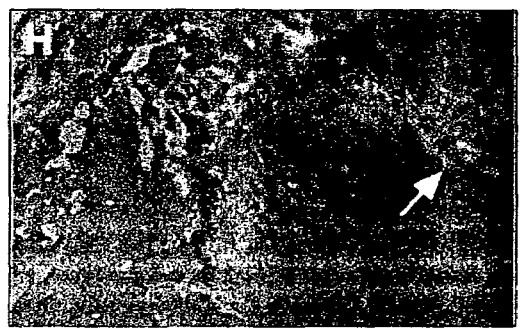

CNS-1 tumor cells were labeled by retroviral transduction with green fluorescent protein (GFP), prior to implantation, to better distinguish single cells away from the main tumor bed [Aboody-Guterman et al., NeuroReport 8: 3801-08, 1997]. GFP-expressing CNS-1 glioma cells ($3 \times 10^4$) in 1 μl PBS injected into right frontal lobe at stereotaxic coordinates 2 mm lateral to bregma, on coronal suture, 3 mm depth from dura. $4 \times 10^4$ C17.2 or TR-10 cells in 1 μl PBS injected at same coordinates directly into tumor bed on day 6. 3-4 C17.2 animals (2 BUdR labeled, 1 BUdR pulsed) and 1-2 TR-10 control animals (1 BUdR labeled). Animals were sacrificed on days 9, 12, 16 and 21 post-tumor implantation. Cryostat sectioned, fixed brain tissue was stained either with 0-galactosidase (C17.2 cells blue) and neutral red (tumor cells dark red) or double immunofluorescence with Texas Red anti-p-galactosidase (C17.2 cells red) and FITC anti-GFP (tumor cells green). FIGS. 3A, 3B show parallel sections: low power of C17.2 cells distributed throughout tumor and surrounding edge (FIG. 3A) X-gal and neutral red (FIG. 3B) double immunofluorescent labeling with Texas red and FITC is (FIGS. 3C, 3D) low and high power of single migrating tumor cell in juxtaposition to C17.2 cell (X-gal and neutral red) is FIGS. 3E and 3F show low and high power magnification of single migrating tumor cell in juxtaposition to C17.2 cell (X-gal and neutral red)(FIGS. 3G, 3H) low and high power of single migrating tumor cells in juxtaposition to C17.2 cells (double immunofluorescent labeling with Texas Red and FITC).

Example 4

NSCs Implanted at Distant Site Migrate Toward Tumor

To examine the capacity of NSCs to migrate through normal tissue and specifically target tumor cells, donor NSCs were injected into uninvolved sites distant from the main tumor bed in three separate paradigms, into the same hemisphere, into the opposite hemisphere, or into the lateral ventricles.

Figure 4C:
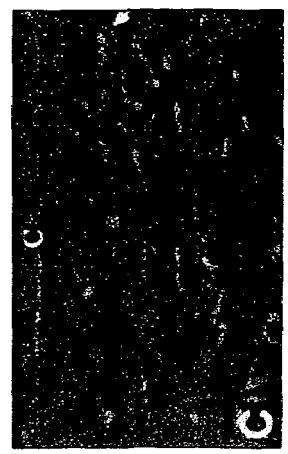
FIGS. 4A, 4B, 4C, 4D, 4E, 4F and 4G illustrate neural progenitor/stem cells implanted at distant site from main tumor bed migrating throughout normal tissue target CNS-1 tumor cells.
Figure 4B:
Figure 4A:
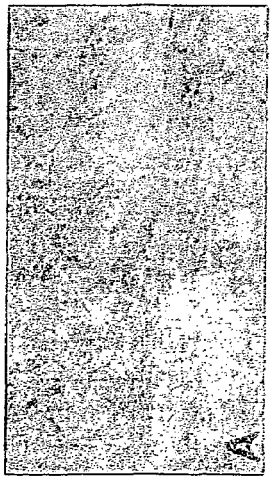

Same hemisphere: CNS-1 glioma cells ($3\times10^4$) in 1 µl PBS was injected into the right frontal lobe at stereotaxic coordinates 2 mm lateral to bregma, on coronal suture, 3 mm depth from dura. $4\times10^4$ C 17.2 or TR-10 cells in 1 µl PBS injected into right frontal parietal lobe at stereotaxic coordinates 3 mm lateral and 4 mm caudal to bregma, 3 mm depth from dura on day 6. Two animals were sacrificed at days 12 and 21. At all time points, NSCs were found distributed within the main tumor bed as well as in juxtaposition to migrating tumor cells in surrounding tissue (FIGS. 4A, 4B).

Figure 4E:
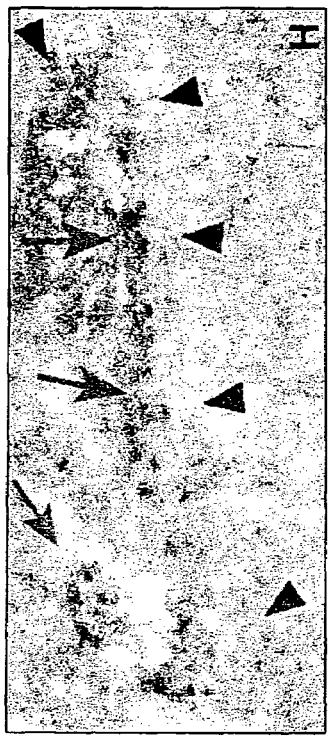
Figure 4G:
Figure 4F:
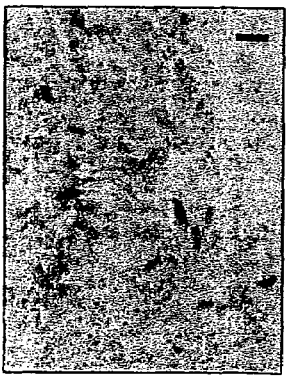
Figure 4D:
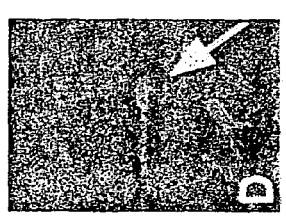

Opposite hemisphere: $3\times10^4$ CNS-1 tumor cells in 1 µl PBS injected into left frontal lobe at stereotaxic coordinates 2 mm lateral to bregma, on coronal suture, 3 mm depths from dura, $5\times10^4$ CNS-1 tumor cells in 1 □l PBS injected into left frontoparietal lobe 3 mm lateral and 4 mm caudal to bregma, 3 mm depth from dura, $8\times10^4$ C17.2 cells in 2 □l PBS injected into right frontal lobe 2 mm lateral and 2 mm caudal to bregma, 3 mm depth from dura on day 6. Two animals sacrificed on day 12 and 21. (control—no tumor Coordinates: 2 mm R of bregma, 2 mm caudal, 3 mm deep). NSCs were seen actively migrating across the central commissure towards the tumor on the opposite side of the brain, and then entering the tumor (FIGS. 4C, 4D, 4E).

Implantation Away from CNS-1 Tumor Bed (Intraventricular):

In this final paradigm $5\times10^4$ CNS-1 tumor cells in I ill PBS was injected into the right frontal lobe 2 mm lateral to bregma, on coronal suture, 3 mm depth from dura. $8\times10^4$ C17.2 cells in 2 µl PBS injected into left or right ventricle I mm lateral and 3 mm caudal to bregma, 2 mm depth from dura on day 6. Two animals sacrificed on days 12 and 21. NSCs again were seen within the main tumor bed, as well as in juxtaposition to migrating tumor cells (FIGS. 4F, 4G). In each case, donor NSCs were found to migrate through normal tissue and "target" the tumor.

Example 5

Effect of Mimosine and GCV Treatment on Cell Number and Morphology of Neural Stem Cells To achieve improved transgene delivery to brain tumor cells infiltrating the brain parenchyma, a novel cell-based delivery system for replication-conditional HSV-1 vectors was developed. This employs neural stem cells, which migrate throughout the tumor and beyond the tumor/parenchyma border, and ribonucleotide reductase-deficient HSV-1 mutants, hrR3 and RRP450, which selectively replicate in dividing cells. Neural stems were infected with virus in culture where viral replication could be reversibly and completely abolished by treatment with mimosine, with reactivation upon removal of mimosine and cell division. Upon in vivo injection of neural stem cells bearing quiescent virus into established intracranial gliomas, virus replication was activated, presumably after some delay. Subsequently, foci of HSV-TK-positive tumor cells were found throughout the tumor and in the surrounding parenchyma. HSV-1-infected tumor cells appeared to be more widely distributed than after direct injection of the same HSV-1 mutant, suggesting an extension of the range of HSV-1 vector delivery using this cell-based delayed activation system.

Co-treatment with GCV as a viral replication block was also tested. After GCV treatment, neural stem cells differentiated into neurons and potentially harbored the virus in a latent state. After withdrawal of GCV and mimosine and splitting of the cultures on day 10, virus titers remained below levels of detection three and six days later. However, viral genomes were shown in infected cells by superinfection with helper virus-free HSV-1 amplicon vectors carrying viral genes known to be involved in HSV-1 action, including the RR-gene and more effectively the RR and VP16 genes. Delivery of VP16 alone was insufficient for reactivation. Thus, it seems crucial to supply high levels of RR expression to guarantee the reentry of the quiescent genome of replication-conditional RR-HSV into the replicative cycle.

Neural stem cell cultures were treated with mimosine (400 µM) and GCV (5 µM) after reaching confluency. Cells/well remained at around 400,000 cells for 4 and 7 days after the beginning of the mimosine treatment. In contrast, untreated neural stem cell cultures continued proliferating over the same period, reaching a density of $1.7\times10^6$ cells/ml on day 10. Additional treatment with 5 µM GCV starting on day 6 after the beginning of mimosine treatment did not significantly affect cell viability, as compared to treatment with mimosine alone. When mimosine alone or mimosine plus GCV were removed on day 10 after the beginning of treatment, growth of neural stem cells resumed. Re-growth of neural stem cells occurred at a faster rate if cells were additionally rinsed and split 1:8 after removal of drug(s) on day 10. Re-growth of neural stem cells also occurred, if cells were kept on mimosine until day 13 and then rinsed and split.

Mimosine-treated cultures of neural stem cells were infected with replication-conditional HSV-1 mutants, hrR3 or RRP450, at an MOI of 1 on day 7 after the beginning of treatment. The genotype of hrR3 is RR-LacZ+ [Goldstein and Weller, *Virology* 166: 141-51, 1988] with the lacZ gene under control of the ICP6 early viral promoter. RRP450 was derived from hrR3 by replacement of the lacZ gene with the cytochrome P450 gene [Chase et al., *Nat Biotechnol* 16: 444-8, 1998]. Virus infection of mimosine-arrested cells at an MOI=1.0 did not affect cell numbers; on day 10, three days after infection, cell numbers in infected and uninfected wells were not significantly different. Infected cultures that were kept on mimosine treatment or mimosine plus GCV treatment remained at the same cell number on day 13 and 17 after the start of treatment. Infection with a higher MOI of 10, however, did lead to a typical cytopathic effect associated with virus replication in mimosine-treated cells, but not in mimosine plus GCV-treated cells. After removal of mimosine or mimosine plus GCV on day 10 and passaging of cultures at a ratio of 1:8, cell numbers increased less rapidly in the mimosine-treated, as compared to the mimosine plus GCV-treated, cultures. Perhaps the mimosine only-treated cultures had more rapid commencement of virus replication than the mimosine plus GCV-treated cultures.

Treatment of neural stem cells with mimosine alone did not induce a significant cytopathic effect. If cells at a density below confluency were treated with mimosine 400 µM, they developed extensions and a more neuronal shape. Additional treatment with GCV did not change this morphology, nor did superinfection of mimosine-treated cultures with RRP450 (MOI=1.0); whereas, infection of untreated cultures virtually wiped out all cells within a few days. Cultures which were previously treated with mimosine, infected on day 7, and split 1:8 into media without mimosine on day 10 showed some cytopathic effect (CPE) on day 13. In contrast, no CPE was seen in uninfected, mimosine-treated and split cultures, infected cultures that had been treated with mimosine and GCV from day 7-10, or mimosine-treated, infected cultures that were not split. On day 17, non-split infected cultures previously treated with mimosine showed some CPE; whereas, mimosine-pretreated, infected and split cultures showed extensive CPE on day 17. By day 17, low level CPE was seen in cell cultures that had been infected and treated with mimosine and GCV. In summary, the presence of mimosine or mimosine plus GCV prevented virally induced CPE; whereas, the removal of these drugs induced CPE. CPE due to virus propagation was greater in proliferating neural stem cells.

Example 6

Figure 7:
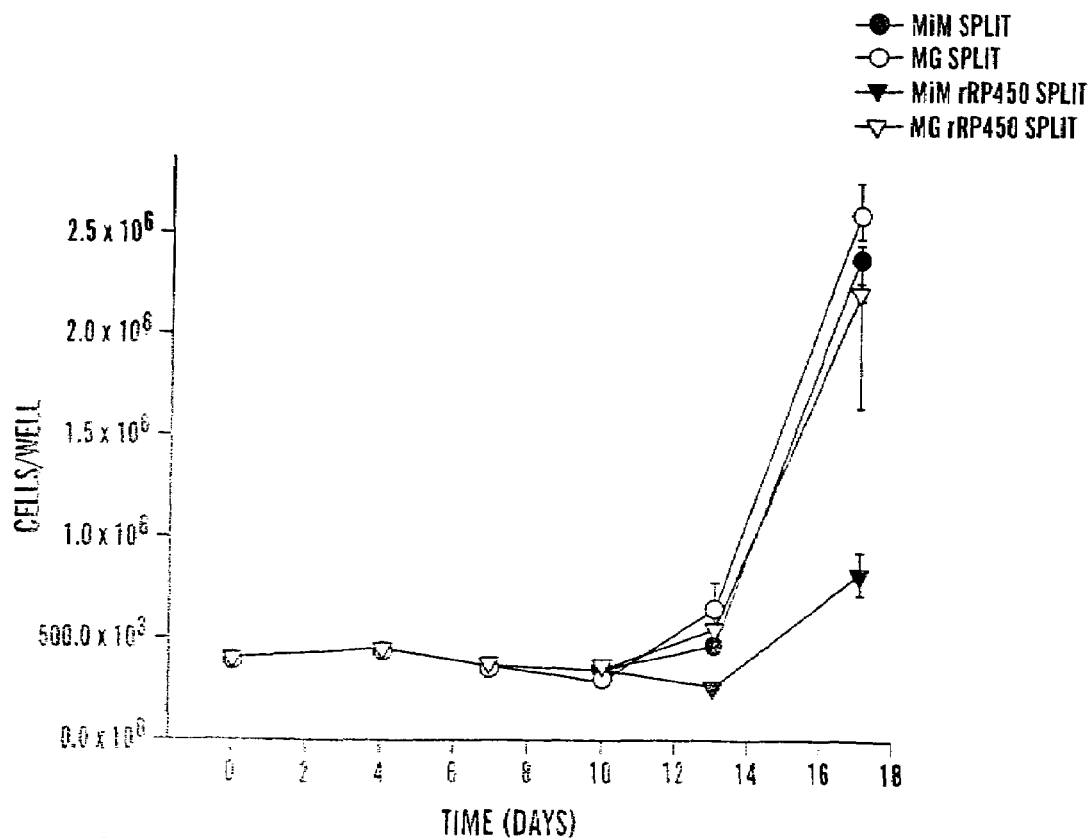
FIG. 7 shows a growth curve of neural stem cells following treatment with mimosine alone or mimosine and GCV which were infected with RRP450 replication-conditional virus at a MOI 1 on day 7.

Effect of Mimosine with and without GCV Pre-treatment on Virus Titers in the Medium of RRP450-Infected Neural Stem Cell Cultures Sub-confluent cultures of neural stem cells were pretreated with 400 µM mimosine for 7 days and then infected with RRP450 at an MOI of 1 ($4 \times 10^5$ pfu/well). Infectious medium was removed and fresh medium containing mimosine was added the day after infection. Some wells were additionally treated with 5 µM GCV one day before infection, and GCV treatment was continued until at least day 10. On day 10, untreated, infected cultures showed a marked cytopathic effect and high titers of virus in the medium, exceeding 10,000 pfu/ml (Table 1). FIG. 7 shows a growth curve of neural stem cells following treatment with mimosine alone or mimosine and GCV which were infected with RRP450 replication-conditional virus at a MOI 1 on day 7.

In contrast, treatment with mimosine and GCV completely abolished virus replication on day 10. Removal of mimosine alone without splitting the cells did not induce detectable replication of RRP450, as measured by pfu in media (Table 1), although some CPE was seen in cells. Removal of mimosine and GCV induced only low level virus replication, 1 out of 8 cell lysates had virus titers of 200 pfu/400,000 cells on day 13 or 17 (Table 1), and some CPE was noted in cultures. However, removal of mimosine with additional splitting of cultures (1:8) induced notable virus replication with some delay: Titers were very low—440 pfU/100,000 cells—

TABLE 1

Titers of RRP450 generated by untreated and drug-treated neural stem cells.

| Day[a] | Treatment[b] | RRP450[c] (pfu/100,000 cells) |
|---|---|---|
| 10 | D10 | >>10,000 |
|  | Min | <10 |
|  | Min + GCV | <10 |
| 13 | Mim removal, not split | <10 |
|  | Mim removal, split 1:8 | 440 +/− 280 |

TABLE 1-continued

Titers of RRP450 generated by untreated and drug-treated neural stem cells.

| Day[a] | Treatment[b] | RRP450[c] (pfu/100,000 cells) |
|---|---|---|
|  | Mim + GCV removal, Split 1:8 | <10 |

[a]Treatment began on day 0. Mimosine and GCV treatment was removed from all cultures on day 10, and some cultures were split 1:8.
[b]Abbreviations: D10 = Dulbecco's modification of Eagle's medium + 10% fetal calf serum + antibiotics; Mim = 400 µM mimosine; GCV = 5 µM GCV.
[c]Cells were infected on day 7 with virus at MOI = 1. Media were harvested on days 10, 13 and 17 after beginning of treatment and assayed virus was titered by plaque assay on 2-2 cells.

Figure 5:
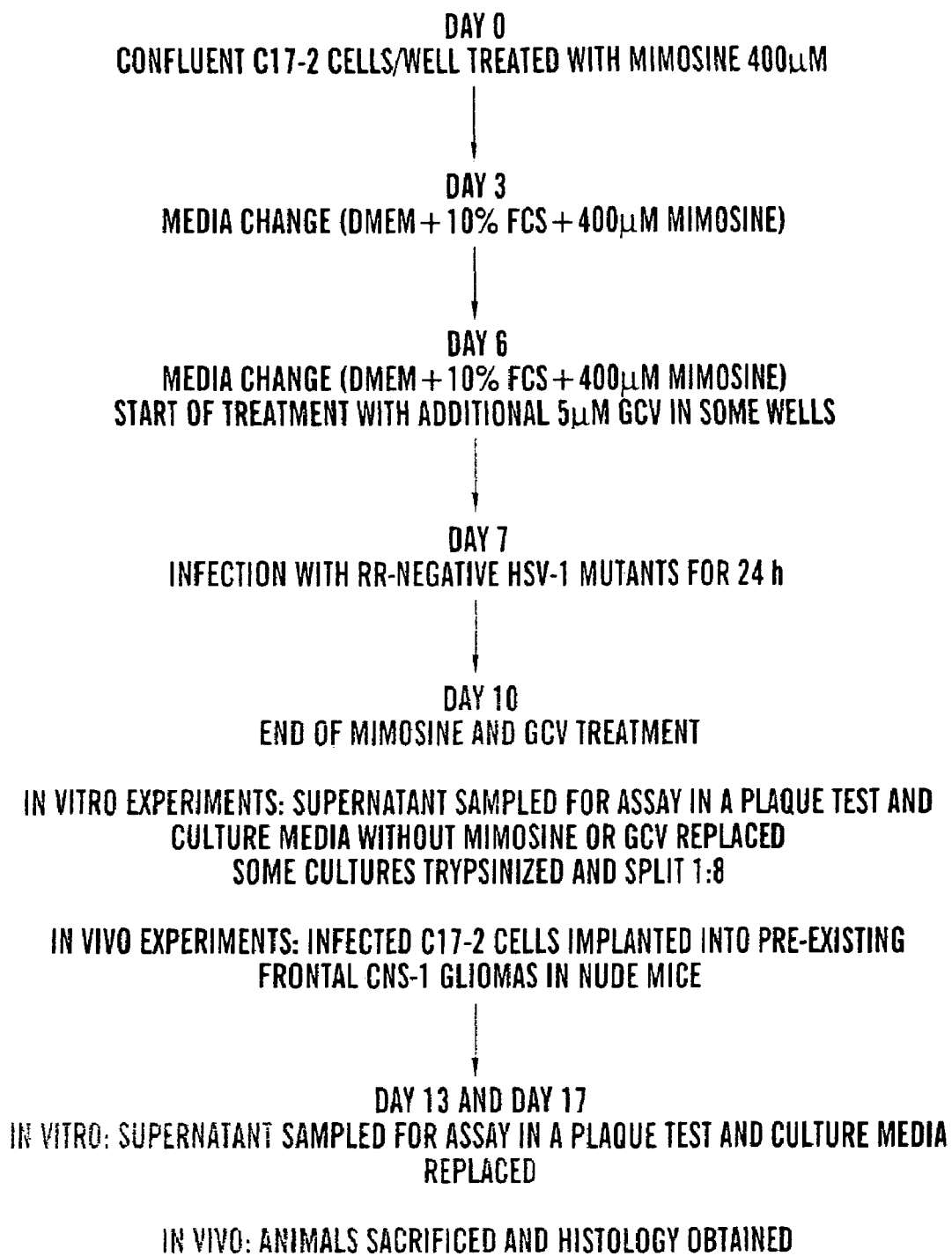
FIG. 5 shows the schedule of drug treatment and superinfection of neural stem cells with ribonucleotide reductase-negative HSC-1 mutants. Early passages of neural stem cells in log-growth phase were gown to confluency (400,000 cells per well in 24-well dish), treated with 400 µM mimosine and 5 µM ganciclovir (GCV), and infected with hrR3 or RRP450 at an MOI of 1. Abbreviations: DMEM is Dulbecco's modified Eagle's medium. FCS is fetal calf serum and RR is ribonucleotide reductase.

3 days after passage (day 13), but increased greatly 7 days after passage (day 17) to 12000 pfu/100,000 cells, i.e. equivalent to 12% of the input virus titer. Thus, using confluent neural stem cells treated with mimosine or mimosine plus GCV, the replication of RRP450 could be suppressed for about 2 weeks and then reactivated in a delayed manner upon removal of drug(s) and splitting of cultures. FIG. 5 shows the schedule of drug treatment and superinfection of neural stem cells with ribonucleotide reductase-negative HSC-1 mutants. Early passages of neural stem cells in log-growth phase were gown to confluency (400,000 cells per well in 24-well dish), treated with 400 µM mimosine and 5 µM ganciclovir (GCV), and infected with hrR3 or RRP450 at an MOI of 1.

Example 7

Stimulation of RR-deficient Virus Replication in GCV/mimosine-Treated Neural Stem Cells by Infection with Amplicon Vectors Expressing lacZ, VP 16, and/or RR To further analyze factors that stimulate reactivation of RR-negative HSV-1 mutants following mimosine/GCV treatment of neural stem cells, cells infected according to the protocol, were subsequently infected with helper virus-free HSV-1 amplicon vectors expressing different virus proteins. Infection of hrR3-infected, growth arrested cells with amplicon vectors on day 7 yielded no titrable virus on day 10, since mimosine and GCV were present during the entire time and blocked virus replication. When mimosine and GCV were removed on day 10 and infection with amplicon vectors was carried out on day 10 or 13, only the vector coding for RR (HSVRR) induced reactivation whereas, vectors VP 16 (HSV 16) and lacZ (HSVlacZ) and the no-vector control did not induce replication in these non-dividing cells (Table 2). The induction of replication by superinfection with an amplicon vector expressing RR was much higher when superinfection was done on day 10 as compared to day 13. This suggests some loss of quiescent HSV-1 DNA during the time of arrested virus replication. On day 10, co-infection with amplicon vectors coding for RR and VP16 markedly enhanced titers >50,000 pfu/ml, as compared to superinfection with RR-amplicon vectors alone. Co-infection with lacZ-expressing amplicon vectors did not enhance titers (Table 2).

In another experiment, neural stem cell cultures treated with mimosine and GCV through day 10 and infected with hrR3 on day 7, were treated on day 10 with dexamethasone $10^{-7}$ M), which is known to be a potent inductor of HSV-1 reactivation; but virus titers in the media and cell lysates remained below detection levels (10 pfu/100,000 cells).

Figure 6:
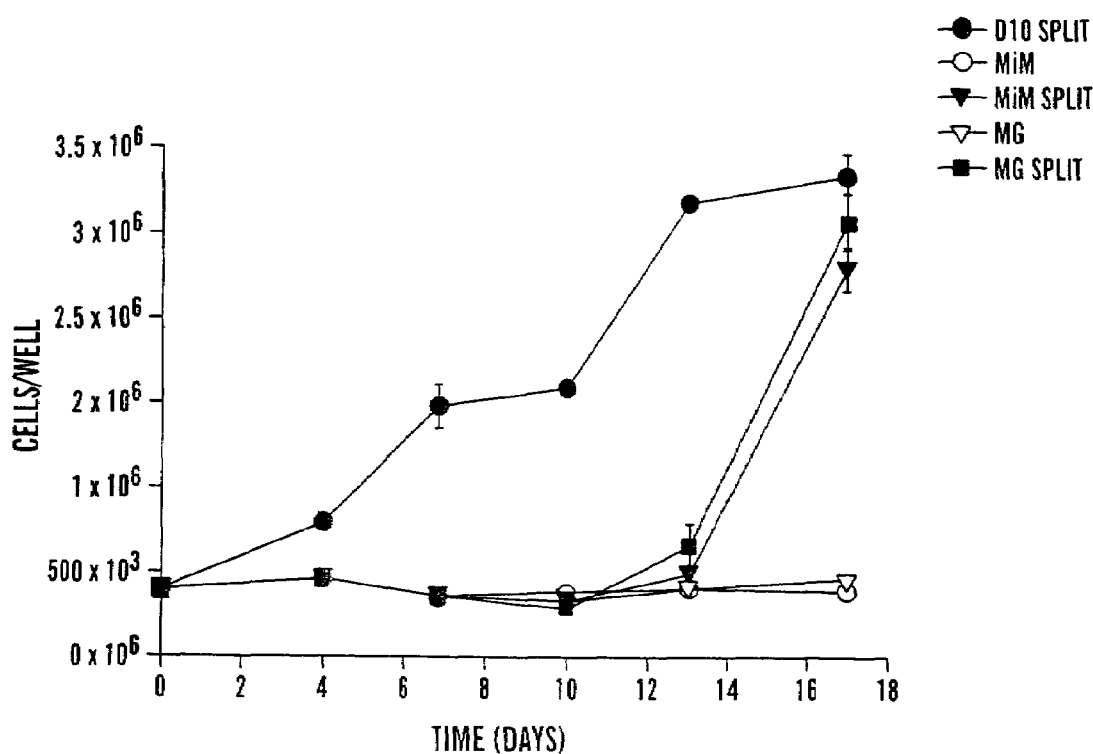
FIG. 6 shows a growth curve of uninfected neural stem cells following treatment with mimosine alone or mimosine and GCV and/or infection with replication-conditional virus. Abbreviations: Mim means cells treated with 400 µM mimosine; MG means cells treated with 400 µM mimosine and 5 µM GCV; split means cell cultures split 1:8 on day 10.

FIG. 6 shows a growth curve of uninfected neural stem cells following treatment with mimosine alone or mimosine and GCV and/or infection with replication-conditional virus. Mim means cells treated with 400 µM mimosine; MG means cells treated with 400 µM mimosine and 5 µM GCV; split means cell cultures split 1:8 on day 10.

Example 8

In Vivo Experiments

One hundred thousand control neural stem cells or cells treated with mimosine plus GCV and infected with RRP450 (MOI 1) were injected on day 10 directly into intracranial CNS-1 gliomas in nude mice. The CNS-1 gliomas had been established by implanting 200,000 CNS-1 cells into the right frontal lobe five days before neural stem cell treatment. Histology of tumor and surrounding brain parenchyma was performed on day 3 and 6 after injection of neural stem cells.

TABLE 2

Titers of hrR3 generated by superinfection of hrR3-infected and drug-treated neural stem cell cultures with helper-free packaged amplicon vectors.

| Day[a] | Amplicon Vector[b] | hrR3[c] titers (pfu/100,000 cells) |
| --- | --- | --- |
| 7 | no vector | 0 |
|   | HSVRR | 0 |
|   | HSV16 | 0 |
|   | HSV16 + HSVRR | 0 |
|   | HSVlacZ + HSVRR | 0 |
| 10 | no vector | 0 |
|   | HSVRR | 2400 +/− 900 |
|   | HSV16 | 0 |
|   | HSV16 + HSVRR | >50 000 |
|   | HSVlacZ | 0 |
|   | HSVlacZ + HSVRR | 2300 +/− 1155 |
| 13 | no vector | 0 |
|   | HSVRR | 15 +/− 5 |
|   | HSV16 | 0 |
|   | HSV16 + HSVRR | 40 +/− 10 |
|   | HSVlacZ | 0 |
|   | HSVlacZ + HSVRR | 20 |

[a]Day of infection with amplicon vector. On day 7 neural system cells treated with mimosine and GCV were infected with hrR3 at MOI 1. On day 10 mimosine and GCV were removed. On days 7, 10, and 13, cultures were infected with 100 µl helper-virus free HSV-1 amplicon vectors carrying the genes for RR (HSVRR), VP16 (HSV 16), or lacZ (HSVlacZ).
[b]HSVRR amplicon construct expresses ribonucleotide reductase under control of the IE4/5 promoter; HSV16 amplicon expresses VP16 under the IE4/5 promoter; and HSV lacZ amplicon expresses *E. coli* lacZ under the IE4/5 promoter.
[c]By standard placque assays, the titer of hrR3 in the media was determined 3 days after superinfection with amplicon vectors or vehicle. "0" is shown if the count was below detection level (<10 pfu/100,000 cells).

At both time points, β-galactosidase staining showed many positive cells in both control and treated neural stem cells throughout the whole glioma. β-galactosidase-positive single cells were also observed invading the CNS parenchyma around the glioma. However, consistent with data in culture the activation of replication of RRP450 in infected cells, as detected by immunohistochemistry of HSV-TK, was low. Only very few HSV-TK positive cells were found on day 3 and 6 after intra-tumoral injection. On sections double stained for HSV-TK and β-galactosidase, most TK-positive cells within the tumor mass were β-galactosidase negative, and thus presumably CNS-1 glioma cells infected with virus released by neural stem cells.

Some neural stem cell cultures had also been treated with mimosine alone, without GCV, and infected with RRP450 at an MOI of 1. Three days after infection, $10^5$ neural stem cells were injected into pre-existing intracranial CNS-1 tumors. Histology was analyzed three days later. Staining with β-galactosidase showed that neural stem cells had migrated throughout the tumor, as described above for the mimosine- and GCV-pretreated cells. However, in this experiment the number of lacZ+ neural stem cells was greatly reduced, as compared to the same number of neural stem cells which had been infected with hrR3 and treated with both mimosine and GCV. The disappearance of lacZ+ neural stem cells can be explained by analogy with experiments in culture in which reactivation and replication of the RRP450 mutant virus subsequently killed host cells. In support of that proposal, HSV-TK immunohistochemistry, used to mark cells actively replicating RRP450, revealed foci of reactivation throughout the glioma. The RRP450 virus delivered by neural stem cells spread not only within the tumor, but also into the brain parenchyma, where single HSV-TK positive cells were found at some distance from the tumor/parenchyma border. Such HSV-TK-positive cells might be single infiltrating neural stem cells in the process of virus reactivation, infected glioma cells, or reactive glial or immune cells. Presumably the TK-positive cells were not neurons, as the RRP450 virus cannot replicate in postmitotic cells.

The efficiency of HSV-TK gene delivery using the neural stem cell/RRP450 delivery system was compared to standard direct injection of $10^5$ pfu of this same virus into an established CNS-1 intracranial tumor. This amount of virus is the same as used to infect the neural stem cells prior to their intratumoral injection and is a more than 100 fold higher than the titer of virus detected in the supernatant of mimosine-treated, RRP450-infected neural stem cells at the time of intracerebral injection (three days after infection, Table 1). Three days after direct injection of the virus, immunohistochemistry showed that HSV-TK+ cells were distributed throughout the tumor. However, after direct virus injection, HSV-TK+ cells were only rarely found beyond the brain/tumor border. This contrasted with gene delivery by the neural stem cell/RRP450 system, following which single HSV-TK+ cells were found some distance outside the tumor/parenchyma border.

What is claimed is:

1. A method of treating a diffuse or metastatic brain tumor in an adult human subject having a diffuse or metastatic brain tumor, said method comprising:
   a) providing a plurality of neuronal stem cells comprising a vector encoding a therapeutic agent; and
   b) intracranially administering said plurality of neuronal stem cells in a pharmaceutically acceptable carrier into a first location in a non-tumorigenic brain tissue of said adult human subject, wherein said plurality of neuronal stem cells migrate from the first location to a second location containing at least one tumor cell and distant from the first location, to specifically target and surround the at least one tumor cell to deliver the therapeutic agent in the vicinity of said tumor cell, and thereby treating the diffuse or metastatic brain tumor.

2. The method of claim 1, wherein the diffuse or metastatic brain tumor is a malignant glioma.

3. The method of claim 1, wherein the vector is deficient for a component necessary for vector replication.

4. The method of claim 3, wherein the component necessary for vector replication is ribonucleotide reductase.

5. The method of claim 1, wherein the diffuse or metastatic brain tumor is a cerebral metastasis from an extracerebral tumor.

* * * * *